US012380995B2

United States Patent
Farren et al.

(10) Patent No.: US 12,380,995 B2
(45) Date of Patent: *Aug. 5, 2025

(54) ARTIFICIAL INTELLIGENCE ENHANCED CLEANING

(71) Applicant: Mynatek, Inc., Oakland, CA (US)

(72) Inventors: Alexander Raymond Richard Farren, Oakland, CA (US); Richard Samuel Kagan, San Jose, CA (US)

(73) Assignee: Mynatek, Inc., Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/671,808

(22) Filed: May 22, 2024

(65) Prior Publication Data
US 2025/0062013 A1    Feb. 20, 2025

Related U.S. Application Data

(63) Continuation of application No. 18/236,824, filed on Aug. 22, 2023, now Pat. No. 12,033,748.

(60) Provisional application No. 63/532,729, filed on Aug. 15, 2023.

(51) Int. Cl.
*G16H 40/20*    (2018.01)
(52) U.S. Cl.
CPC .................................. *G16H 40/20* (2018.01)
(58) Field of Classification Search
CPC ...................................................... G16H 40/20
See application file for complete search history.

(56) References Cited

U.S. PATENT DOCUMENTS

| 2018/0122506 A1 | 5/2018 | Grantcharov |
| 2023/0120290 A1* | 4/2023 | Baarman ............... G16H 10/65 15/3 |

FOREIGN PATENT DOCUMENTS

| CN | 112239120 | 1/2021 | |
| CN | 112239120 A * | 1/2021 | ............... A61L 2/10 |
| WO | 2022101860 | 5/2022 | |

OTHER PUBLICATIONS

Bjorlykhaug, Emil and Olav Egeland. Vision System for Quality Assessment of Robotic Cleaning of Fish Processing Plants Using CNN. IEEE Access. vol. 7, 2019 (Year: 2019).*
Bjorlykhaug et al., "Vision System for Quality Assessment of Robotic Cleaning of Fish Processing Plants Using CNN". IEEE Access. vol. 7, 2019 (Year: 2019).
Mckinley et al., Evaluation of Daily Environmental Cleaning and Disinfection Practices in Veterans Affairs Acute and Long-Term Care Facilities: A Mixed Methods Study, American Journal of Infection Control, Feb. 2023, vol. 51, Issue 2.
Singh et al., Automatic Detection of Hand Hygiene Using Computer Vision Technology, Journal of the American Medical Informatics Association, 2020, vol. 27 Issue 8.

(Continued)

*Primary Examiner* — Linh Giang Le
(74) *Attorney, Agent, or Firm* — Van Pelt, Yi & James LLP

(57) ABSTRACT

A plurality of surfaces within a space are monitored in real-time during a cleaning of the space utilizing data outputted from the plurality of sensors. Computer vision is utilized to determine one or more surfaces of the plurality of surfaces that need additional cleaning based the real-time monitoring of the plurality of spaces. A notification of the one or more determined surfaces that need the additional cleaning is provided.

20 Claims, 19 Drawing Sheets

(56) References Cited

OTHER PUBLICATIONS

Uppal et al., "Cloud-Based Fault Prediction Using IoT in Office Automation for Improvisation of Health of Employees", Chitkara University Institute of Engineering and Technology, Chitkara University, Journal of Healthcare Engineering, vol. 2021, Hindawi Limited, 2021, 2 pages.

* cited by examiner

| Surface ID | Coordinates (x,y,z) |
|---|---|
| IV Pump | 2,1.5,2 |
| Keyboard | 3.5,1.7,3.1 |
| Overbed table | 2.5,1.2,2.7 |
| Bed frame rails | 2.1,1.4,2.3 |

ARTIFICIAL INTELLIGENCE ENHANCED CLEANING

CROSS REFERENCE TO OTHER APPLICATIONS

This application is a continuation of U.S. patent application Ser. No. 18/236,824 entitled ARTIFICIAL INTELLIGENCE ENHANCED CLEANING filed Aug. 22, 2023, which claims priority to U.S. Provisional Patent Application No. 63/532,729 entitled ARTIFICIAL INTELLIGENCE ENHANCED CLEANING filed Aug. 15, 2023, each of which is incorporated herein by reference for all purposes.

BACKGROUND OF THE INVENTION

"To err is human." This old phrase applies to many human activities. One of those is cleaning. A number of institutions make use of cleaning crews. These include business offices, museums, hotels, airports, hospitals, etc.

In 2023 Safdar et al. published an article entitled "Evaluation of daily environmental cleaning and disinfection practices in veterans affairs acute and long-term care facilities: A mixed methods study," which disclosed that:

Overall observed rates of daily cleaning of environmental surfaces in both acute and long-term care was low. Standardized environmental cleaning practices to address known barriers, specifically cleaning practices when patients are present in rooms and semi-private rooms are needed to achieve improvements in cleaning rates. The average observed surface cleaning rate during daily cleaning in patient rooms was 33.6% for all environmental surfaces and 60.0% for high-touch surfaces (HTS). Higher cleaning rates were observed with bathroom surfaces (Odds Ratio (OR) =3.23), HTSs (OR=1.57), and reusable medical equipment (RME) (OR=1.40). Lower cleaning rates were observed when cleaning semiprivate rooms (OR=0.71) and rooms in AC (acute care) (OR=0.56). In analysis stratified by patient presence (i.e., present, or absent) in the room during cleaning, patient absence was associated with higher cleaning rates for HTSs (OR=1.71). In addition, the odds that bathroom surfaces being cleaned more frequently than bedroom surfaces decreased (OR=1.97) as well as the odds that private rooms being cleaned more frequently than semi-private rooms also decreased (OR=0.26; 0.07-0.93).

This demonstrates, among other things, that when patients are present within a space, cleaning is less effective. Indeed, human cleaning crews, even in hospitals, are prone to error as has been shown in a 2020 Stanford study that focused on hand washing. According to the study:

Hand hygiene of hospital staff is notoriously difficult to monitor, yet few behaviors are as essential to patient health. . . . Researchers from Stanford's Partnership in AI-Assisted Care (PAC) installed sixteen depth sensors in the ceiling above wall-mounted hand hygiene dispensers outside patient rooms. . . . The system . . . accurately determines whether [human cleaners] use the handwashing dispenser when they enter and exit the room. Automatic detection of hand hygiene using computer vision technology, Journal of the American Medical Informatics Association, Volume 27, Issue 8, August 2020, Pages 1316-1320

The study showed that AI monitoring of hand-washing improved compliance of the cleaning crews in washing their hands. A similar improvement is needed for human crews that clean the surfaces of items in a partially or completely enclosed space.

This is especially the case for hospital rooms or other environments—a place where proper cleaning can mean the difference between health and illness. In hospital settings, according to the CDC, cleaning a room involves three steps: (1) cleaning, (2) sanitizing, and (3) disinfecting. Prior to disinfecting a surface, the cleaner must clean the surface of organic materials that would impede or reduce the efficacy of the disinfectant. This cleaning is typically performed by mechanical action applying a chemical cleaner; for example, a cleaner wiping down a surface with a cloth or wipe that has been soaked with a chemical cleaner. Sanitizing is performed similarly.

Once the surface is deemed free of all debris and many pathogens, chemical disinfectants can be applied in a similar manner—that is, cleaners using ready-to-use wipes that are pre-soaked with disinfectants. The EPA considers chemical disinfectants (a) to be effective and in compliance with use regulations only when applied to a clean surface free of organic matter, and further, (b) effectively applied only with specific contact times.

If automated means of disinfection are applied, such as steam, UVC, pulsed UV, or Blue light (germicidal lamps), such means must also be applied to a cleaned and sanitized surface.

FIG. 1 depicts a cleaning crew in a hospital room 100. Cleaner 110 is one of three cleaners in room 100. Cleaner 110 is helping to clean surface 120 using his right hand 111. In his right hand 111 is rag 130 soaked in a disinfectant solution 131. Solution 131 is present on a section of surface 120 near the right hand 111, given that cleaner 110 has recently wiped that area with rag 130.

However, cleaner 110 has missed area 121 on the side of surface 120. If the cleaning crew leaves room 110 to head to the next room to clean with area 121 not having been cleaned, this represents an unfortunate consequence of human cleaning that can lead to a dangerous condition for the patient in room 100.

FIG. 2 depicts room 100 including UV device 210. UV device 210 disinfects room 100 of pathogens using UV light. However, an unfortunate consequence of using a UV device to kill pathogens in a room is that the UV dose delivered by a UV device, such as UV device 210, varies within different areas of a room, such as room 100. For example, area 211 receives the highest UV dose and area 212 receives the lowest UV dose. Area 212 represents an unfortunate consequence of using UV devices to disinfect since UV light dose decreases with increasing distance from a center point associated with a field of illumination, and space and money interests limit the number of such devices in a room.

FIG. 3 shows a doctor 320 and a nurse 330 in room 100 and their common walking path 310. Unknowingly, humans, such as doctor 320 and nurse 330, potentially, carry pathogens on the soles of their shoes that they picked up outdoors or in other indoor areas, as well as on their unwashed hands and their clothes or other items that they may bring into room 100. When people with such pathogens on the bottoms of their shoes walk into room 100, and touch fixtures with their unwashed hands, they can deposit these dangerous cells on the floor and one the fixtures. FIG. 3 also shows surface 311—the keyboard of a computer—which experiences high hand touch frequency.

The common thread of all three of the foregoing situations, i.e., missed areas of cleaning crews, areas receiving low or no doses of UV light, and human foot traffic areas and hand touched surfaces, is that these areas need to be cleaned and disinfected thoroughly.

BRIEF DESCRIPTION OF THE DRAWINGS

Various embodiments of the invention are disclosed in the following detailed description and the accompanying drawings.

FIG. 8 depicts a table comprising rows of coordinates in accordance with some embodiments.

DETAILED DESCRIPTION

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

Figure 1:
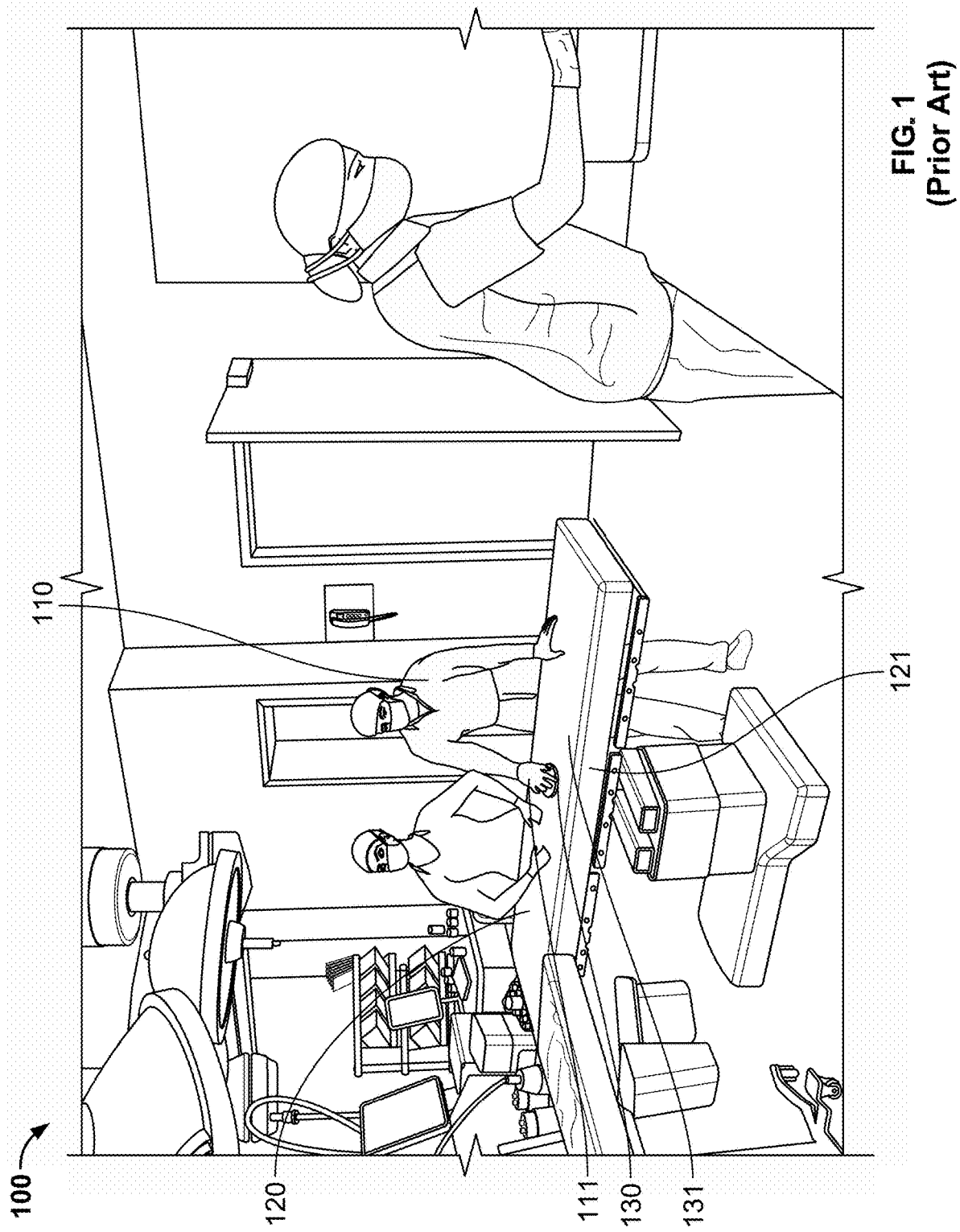
FIG. 1 depicts a cleaning crew in a hospital room.
Figure 2:
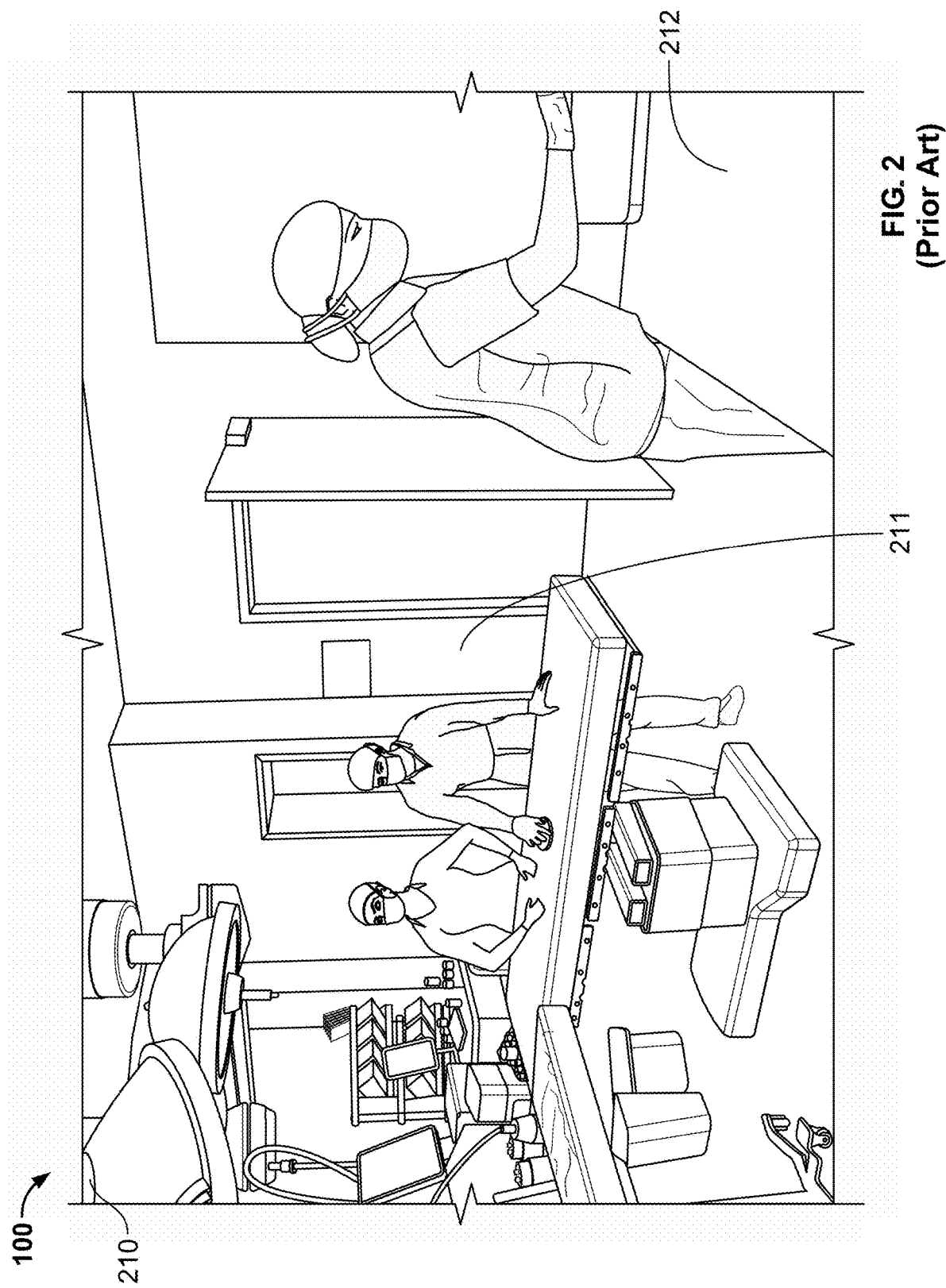
FIG. 2 depicts a room that includes a UV device.
Figure 3:
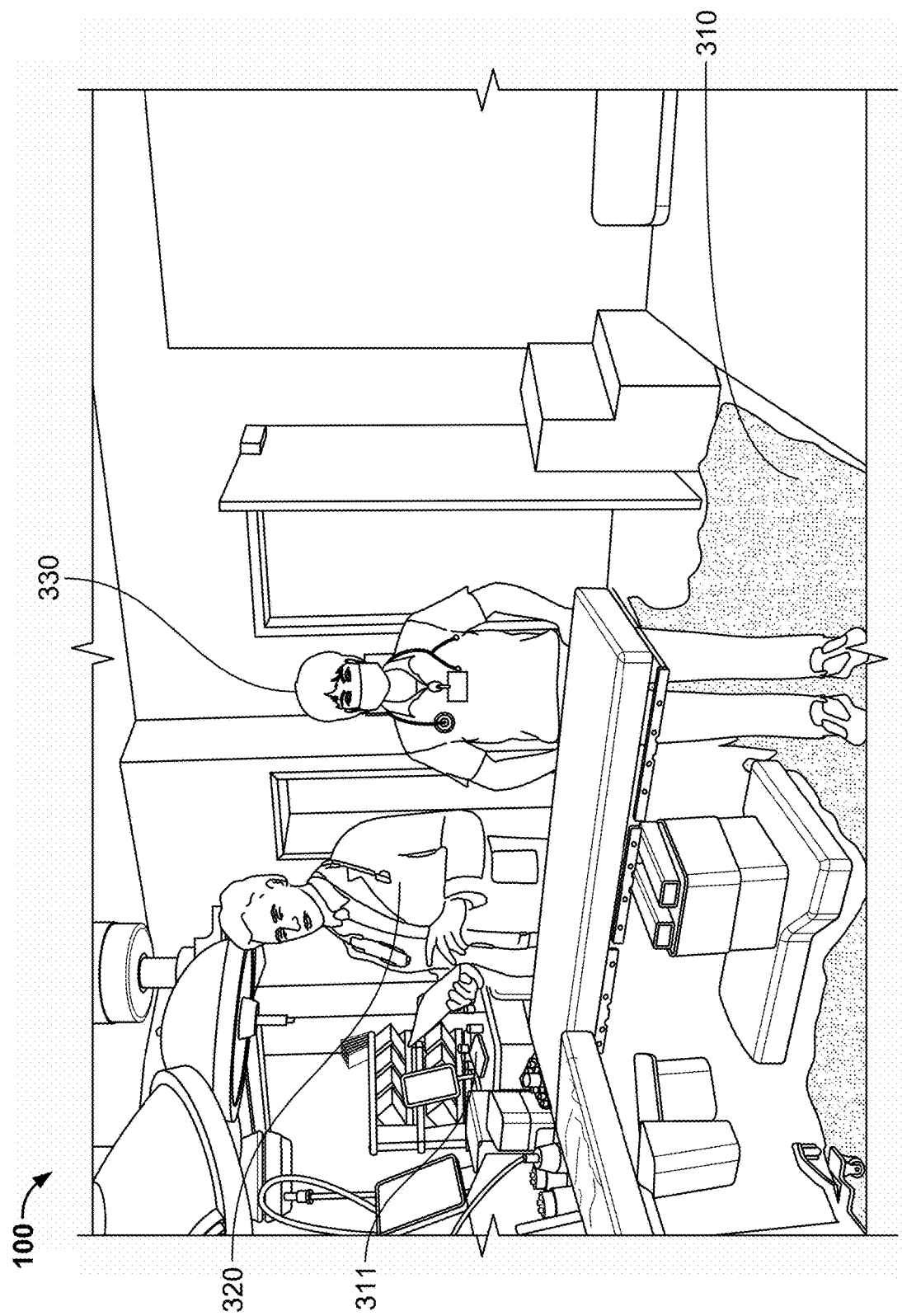
FIG. 3 depicts a doctor and a nurse in a room and their common walking path.

Artificial intelligence ("AI") is the simulation of human intelligence processing performed by machines. Computer vision is a set of technologies known in the art for providing automatic image-based identification of people, objects, surfaces, and their x,y,z coordinates within a field of view, such as the view of room 100 of FIG. 1. Deep learning algorithms using layered neural networks or other types of machine learning algorithms can take the data provided by the computer.

AI and computer vision are two closely related fields that intersect to enable machines to perceive and understand visual information. Computer vision refers to the ability of computers or machines to extract meaning from images or videos, similar to how humans interpret visual data. AI, on the other hand, focuses on executing algorithms and models that can learn from data and make intelligent decisions or predictions.

When AI and computer vision technologies combine, they open up a wide range of applications and possibilities, such as:

1. Image/Video Acquisition: The process starts with capturing visual data through cameras or sensors. These images or videos serve as input for a computer vision system.

2. Preprocessing: Raw visual data often requires preprocessing to enhance image quality, remove noise, correct distortions, or adjust lighting conditions. Preprocessing techniques may involve resizing, filtering, or transforming the data.

3. Feature Extraction: Computer vision algorithms analyze the visual data and extract relevant features or patterns. These features could include edges, shapes, textures, colors, or even more complex visual characteristics. These features serve as inputs to AI algorithms.

4. Machine Learning: AI algorithms, such as deep learning models, are trained on labeled datasets to learn patterns and relationships between the extracted features and the corresponding labels or annotations. The training process involves presenting the AI algorithm with a large number of labeled examples to optimize the model's parameters to learn the relationships between the input features and the corresponding labels or annotations, allowing it to generalize and make predictions or classifications on new, unseen data. This training enables the model to recognize patterns, objects, or scenes within visual data.

5. Object Detection/Recognition: Once the model is trained, it can be applied to identify and locate specific objects or regions of interest within images or videos. Object detection algorithms can identify and outline multiple objects simultaneously, while object recognition algorithms can classify the detected objects into specific categories. AI provides the intelligence to make accurate predictions and improve the overall accuracy of object detection and recognition systems.

6. Scene Understanding: AI and computer vision systems can go beyond simple object detection and recognition. They may collaborate to achieve higher-level scene understanding. For example, they can analyze the overall scene, interpret the relationships between objects, and understand the context in which they appear. This higher-level understanding allows the system to make more informed decisions or provide meaningful insights.

7. Applications: AI and computer vision have diverse applications across various domains. Some examples include autonomous vehicles, facial recognition, medical imaging, surveillance systems, augmented reality, robotics, quality control in manufacturing, and more.

8. Real-time Processing: AI and computer vision can work together to achieve real-time processing of visual data. This is crucial for applications such as autonomous vehicles, surveillance systems, or robotics, where immediate analysis and decision-making are required. The combination of AI's ability to learn and adapt and computer vision's fast processing capabilities enables real-time responses to visual stimuli.

9. Continuous Learning: AI algorithms can continuously learn and improve from new visual data, allowing the system to adapt and enhance its performance over time. Computer vision provides a constant stream of visual input for the AI model to learn from, enabling the system to become more accurate and robust as it encounters new scenarios and data.

10. Application-Specific Solutions: AI and computer vision are employed together to develop application-specific solutions. For example, in medical imaging, AI algorithms analyze medical scans with the help of computer vision techniques to detect anomalies or assist in diagnosis. Similarly, in autonomous vehicles, computer vision systems capture and process the environment's visual data, while AI algorithms interpret and make decisions based on that data.

Overall, AI and computer vision may collaborate to create intelligent systems capable of perceiving, understanding, and acting upon visual information. The combination of AI's learning capabilities and computer vision's visual processing expertise empowers machines to perform complex tasks, replicate human vision to a certain extent, and open up new possibilities in various domains.

One of the core technologies used for computer vision is a digital camera which can be composed of a lens to capture the light, visible light, infrared, UV light, or other wavelengths, and project it on a camera sensor and capture board (also known as frame grabber or more generally as a sensor) to convert the captured light into a digital format such as pixels or electric signals. A processor runs algorithms to process the image and extract the desired information. There are multiple types of camera sensors used in computer vision such as CCD, CMOS, microbolometers and FPA sensors. Different cameras often have different resolution and sensitivity.

"Computer vision" is sometimes used synonymously with "machine vision," however, the latter is usually associated with more powerful processors taking a longer time to analyze an image. Computer vision does not always use a camera as images can be transferred electronically in the form of files.

Machine vision is typically used for higher throughput industrial operations and can use wavelengths that are not visible to the human eye such as infrared, UV or x-rays. Machine vision is usually tasked to perform image analysis more rapidly. Computer vision can use sensing output from a variety of sensors such as cameras, lidar, various forms of radar such as mm wavelength radar and other sensing technologies.

In some embodiments, computer vision is employed. In other embodiments, machine vision is employed. In some embodiments, a combination of computer vision and machine vision is employed. In some embodiments, a camera device employing computer and/or machine vision is implemented as an independent fixture, or included within a larger device, such as device 400.

Figure 4A:
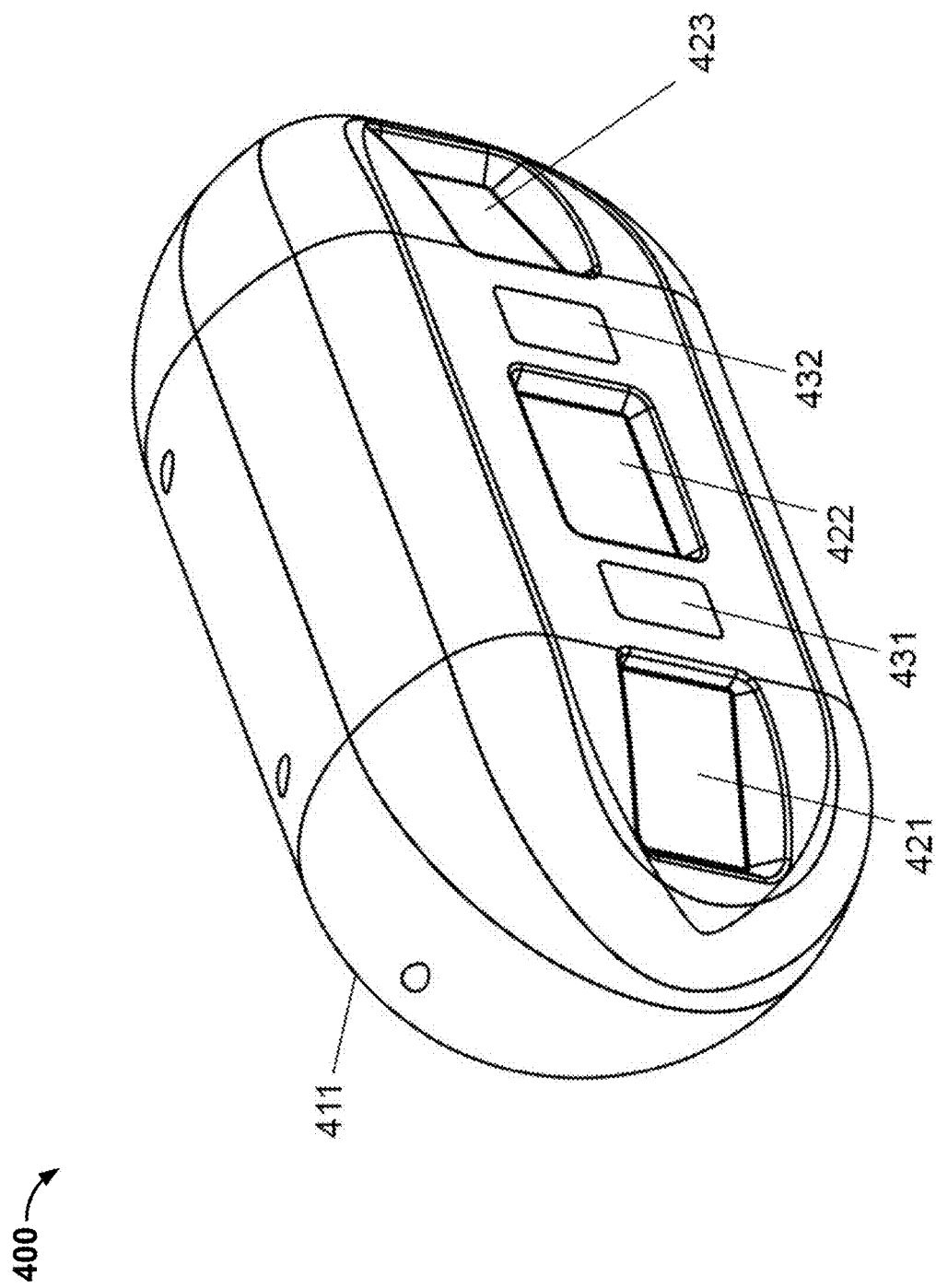
FIG. 4A is a diagram illustrating a UV device that shines UV light as well as providing the computer vision capability in accordance with some embodiments.

FIG. 4A is a diagram illustrating a device for AI enhanced cleaning in accordance with some embodiments. In the example shown, device 400 includes enclosure 411, UV lamps 421, 422, and 423, and camera sensors 431 and 432. Although FIG. 4 depicts device 400 having three UV lamps, device 400 may include 0:n UV lamps. Although FIG. 4 depicts device 400 having two camera sensors, device 400 may include 1:n camera sensors.

In some embodiments, UV lamps 421, 422, and 423 are Ushio B1 narrow beam modules. These modules, produced by Ushio, are filtered KrCl excimer lamps with a field of irradiance of 60 degrees, input power of 11 W, and lamp voltage of 4-6V. UV output at the center of irradiance at 1 m is 14 uW/cm^2. Other types of lamps may be used for UV lamps 421, 422, and 423. UV lamps 421, 422, and 423 may be battery powered, plugged into a wall outlet, powered via power over Ethernet, or powered by any other power source.

In some embodiments, camera sensors 431 and 432 are Seeed Studio IMX219-160 8MP cameras with a 30 frames/s frame rate and a field of view of 160 degrees. Other types of camera sensors having different frame rates and field of views may be used. Camera sensor 431 may have a different frame rate and/or a different field of view than camera sensor 432. A single camera sensor can be used to detect and identify people, and two camera sensors can be used on a device to operate stereoscopically and determine coordinates of occupants in a space. A person may be identified based on one or more characteristics, such as the detection of a face, gait, body shape, temperature, or other characteristic. In some embodiments, camera sensors 431 and 432 include the ability to function in the dark, using, for example, infrared light.

Each of the UV lamps 421, 422, 423 has a corresponding field of illumination. In some embodiments, the field of illumination associated with a UV lamp overlaps with the field of illumination associated with at least one other UV lamp. In some embodiments, the field of illumination associated with a UV lamp does not overlap with the field of illumination associated with any of the other lamps of device 400. Different levels of light can be emitted by different UV lamps depending on whether or not their field of illumination includes people. For UV lamps for which their field of illumination does not include one or more people, the defined limit of UV light for people can be exceeded; for lamps with fields that include one or more people, the limit is adhered to.

Computer Vision of Areas

Figure 4B:
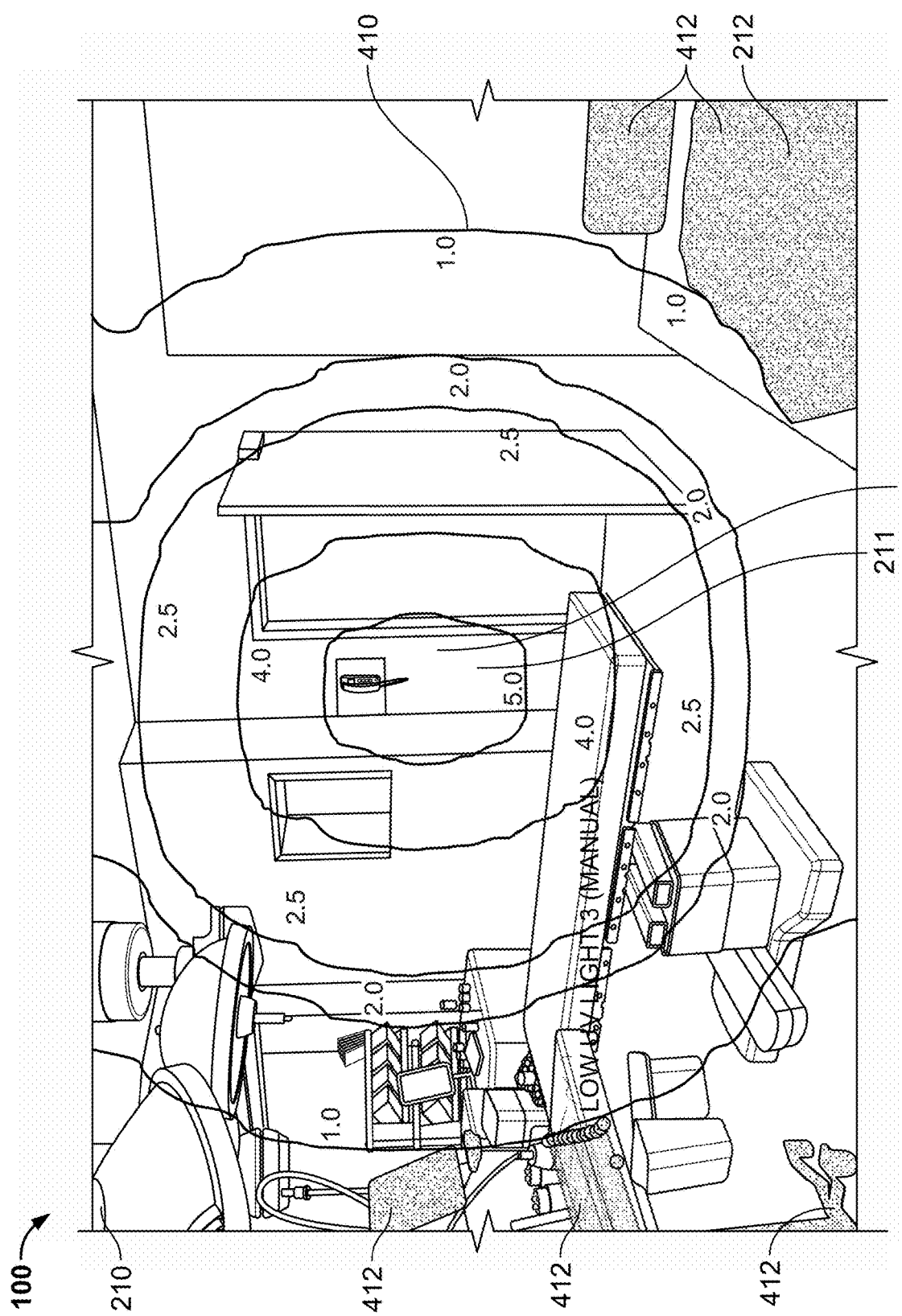
FIG. 4B depicts a computer-generated image of UV light doses in a plane at a certain distance from the UV light source in accordance with some embodiments.

FIG. 4B depicts a computer-generated image of UV light doses in a plane at a certain distance from the UV light source in accordance with some embodiments. UV light reaches area 410, which is the area that one of the three UV lights of device 400 may reach. Area 410 comprises roughly circles within other circles. The smallest and center area 411 within area 410 represents the highest dose of UV light in this area. The largest and most outside area 410 represents the lowest dose of UV light in this area.

FIG. 4B shows the parts of fixtures 412 that are within area 410 shaded so these low dose parts are easily identified. The foregoing lowest dose fixtures outside of area 410 need human cleaning crews to focus on them since they are most likely to contain pathogens that the UV light did not inactivate.

Figure 5:
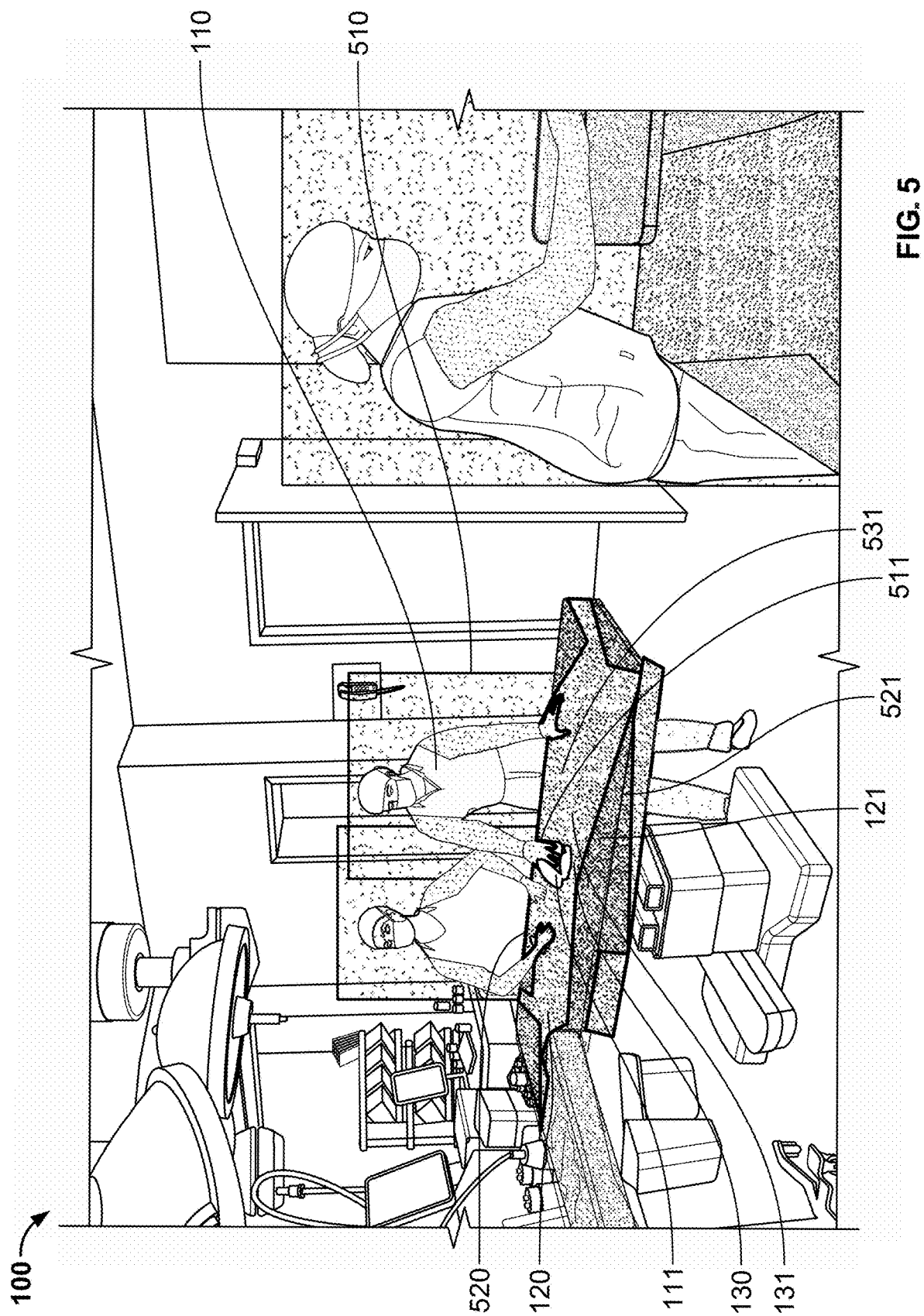
FIG. 5 depicts a computer vision of a human cleaning crew in the midst of cleaning room in accordance with some embodiments.

FIG. 5 depicts a computer vision of a human cleaning crew in the midst of cleaning room 100 in accordance with some embodiments. Although room 100 is depicted as a hospital room, room 100 may be an elevator, a waiting area, a hallway, a restaurant, a car, a train, a grocery store, a gym, a studio, a place of worship, a theater, or other any human occupied space. The computer vision detects the three members of the crew within room 100. For example, computer vision draws box 510 around cleaner 110. Computer vision further draws hand shape 511 around hand 111 of cleaner 110. Computer vision also draws shape 520 around surface 120 which two of the crew (including cleaner 110) are currently cleaning.

Computer vision tracks the movement of shape 511 (cleaner 110's hand) over shape 520 and records the locations within shape 520 that shape 511 has swiped with rag 130. Computer vision performs the same tracking and recording for all three members of the crew.

Once the crew has finished cleaning and leaves room 100, computer vision can identify the areas of shape 520 that no shapes 511 (e.g., hands) have wiped. Shape 521, drawn by computer vision, represents area 121 that the cleaning crew missed.

The cleaning crew needs to return to room 100 to clean the areas that it missed, such as shape 521 (i.e. area 121).

In an embodiment, computer vision is used to rate the quality of the overall cleaning effort. For example, a model that informs the computer vision may be trained using videos of thorough and effective cleaning in contrast to ineffective cleaning. This could be true not only for a task such as surface cleaning, but also for hand washing, floor cleaning, linen replacements, trash removal, and other such activities.

The model might also be trained on a full complement of typical room cleaning processes, with the output of the model predicting the overall effectiveness of the effort. For example, the output of the model could be the following: after the cleaning routine, the probability of surface pathogen levels above x amount is y percent. This estimate could also be tied to what the system has observed in the room previous to the cleaning. For example, factors that the model may consider include: an amount of time since a previous cleaning, a number of patients in the room since a previous cleaning, a duration in which a patient was in the room, a number of staff that has passed through the room since a previous cleaning, a duration in which each staff member was in the room, a number of cleaning measures that were applied, etc.

In some embodiments, the amount of activity in a particular area since a last cleaning is tracked. A particular area may include a bathroom, sink, or surface. Such data is used to provide information to a cleaning crew before they begin, potentially increasing the effectiveness of their work.

In some embodiments, the cleaning crew uses a disinfecting solution that contains an invisible dye that can be picked up by a camera device. For example, the company GLO Effex sells a product it calls "Invisible Blue UV Reactive Water Dye." This water-soluble dye glows with a UV blacklight.

Figure 6:
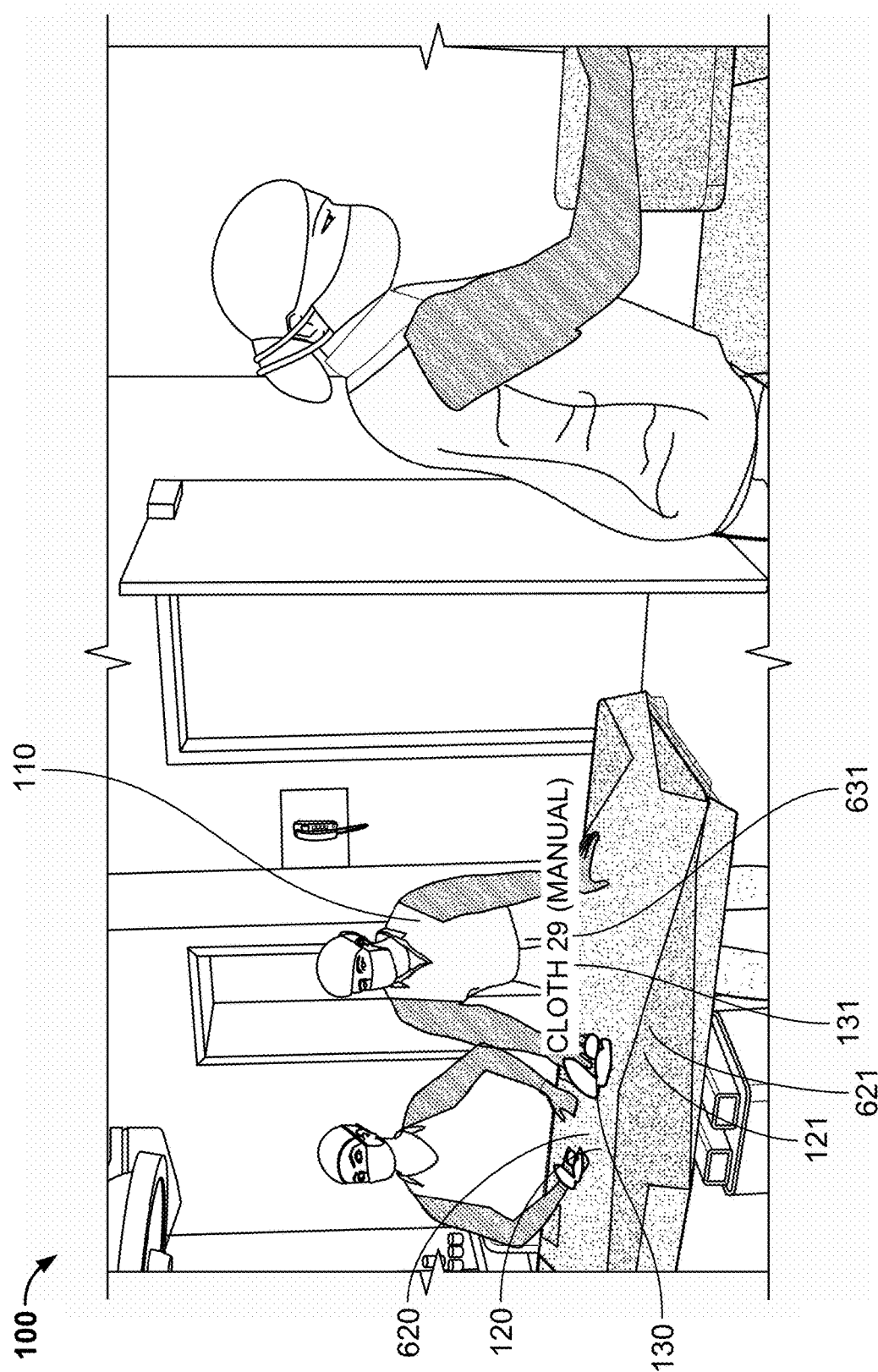
FIG. 6 shows a human cleaning crew in the midst of cleaning using a disinfecting solution that includes invisible dye in accordance with some embodiments.

FIG. 6 shows a human cleaning crew in the midst of cleaning using a disinfecting solution that includes invisible dye in accordance with some embodiments. All three members of the crew are using this solution in their cleaning of room 100. For cleaner 110, the UV light shows the invisible dye 631 being present at area 131 that cleaner 110 has recently wiped. The UV light also shows no invisible dye 621 present on area 121 that the crew missed.

Once the crew has finished cleaning room 100, UV light can identify all the areas that the cleaning crew missed, namely, the areas revealing the absence of invisible dye. The cleaning crew needs to return to room 100 to clean the areas that it missed, such as dye-less area 621 (i.e., area 121).

Figure 7:
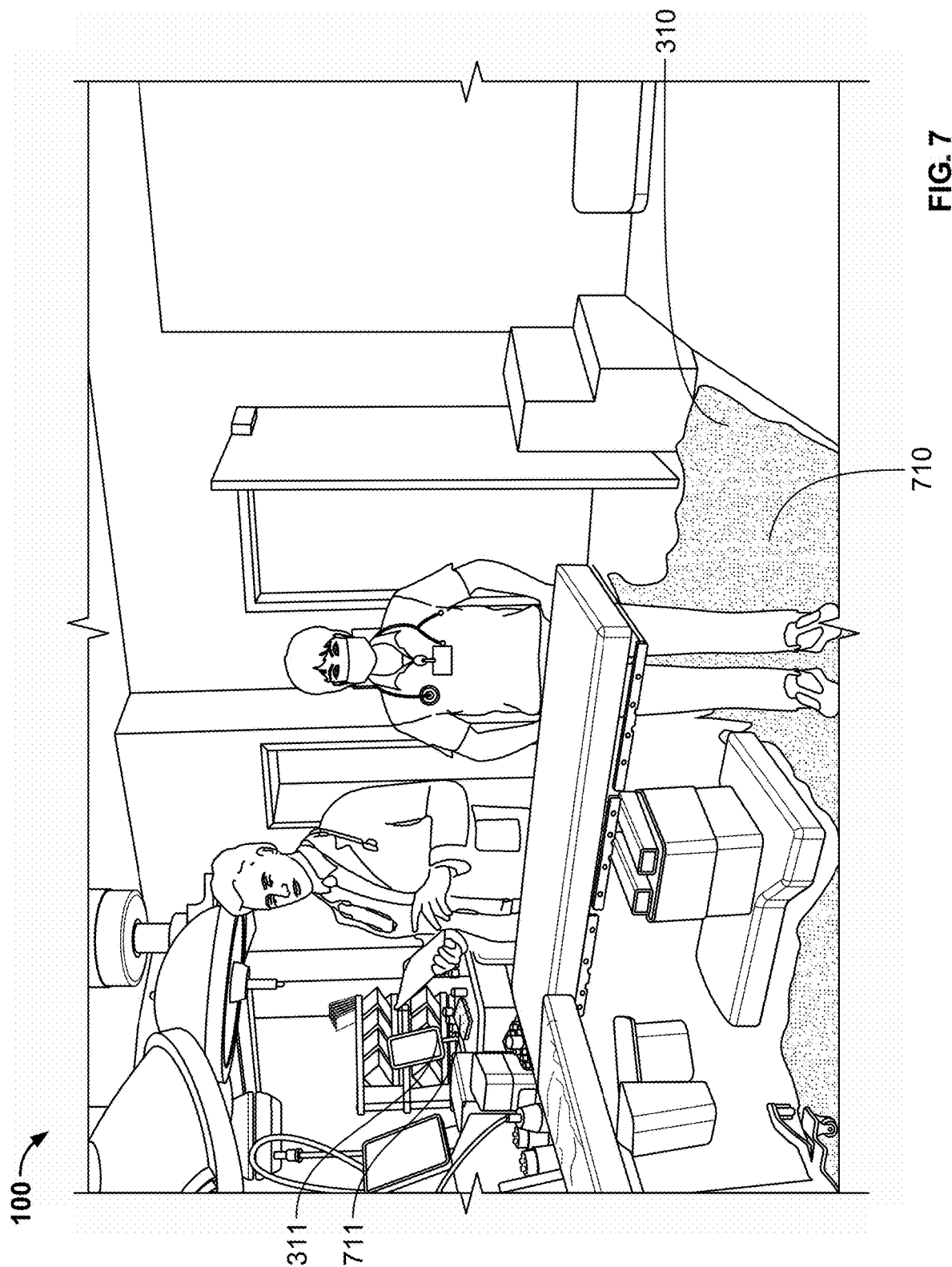
FIG. 7 shows a computer vision of human traffic paths in accordance with some embodiments.

FIG. 7 shows a computer vision of human traffic paths in accordance with some embodiments. Area 710 corresponds to the main path 310 of traffic. Surface 711 corresponds to a frequently touched fixture. The cleaning crew needs to return to room 100 to clean the areas of heavy foot traffic and hand touch, such as areas 710 and 711.

In some embodiments, thermal cameras are used to detect which surfaces have been wiped by recognizing the difference in temperature between wiped surfaces with chemical cleaners or disinfectants and non-wiped surfaces. Rates of temperature change on wiped surfaces can also be used to determine volume and contact time of disinfectant and cleaners and whether the contact time was sufficient. Wet surfaces will generally appear cooler than dry surfaces and can be segmented by the computer vision.

In some embodiments, the computer vision of human traffic paths is employed for a second purpose: to guide the on/off patterns of the UV device 210. In such embodiments, the locations of heavy foot and hand traffic are not only tracked, but also of the time periods of this traffic.

For example, the system records that, on weekdays, heavy traffic begins around 8 am. The system knows the number and positions of the UV devices in the area of this traffic, and calculates how many minutes (e.g., 32 minutes) it would take for these UV devices to cause a significant reduction (e.g. 3 log) of pathogens in the area. The system uses that calculation to turn on the UV lights that many minutes (e.g., 32 minutes) before 8 am.

In some embodiments, patients that are infected with a pathogen are identified by utilizing data received from the hospital. Healthcare workers that visit this patient can also be identified using computer vision. The movement of and surfaces touched by both the healthcare worker and the patient (for example the patient would move if taken to get an MRI) can be tracked wherever camera devices are present. This can be used to establish movement patterns and even provide potential information on the spread of infection either from the patient directly or by the healthcare worker who acquired the pathogen from surfaces within the original patient's room or from the patient and then, for example, contacted other patients within the facility. Also, said areas and surfaces are identified as priority places needing disinfecting.

In some embodiments, computer vision is used to perform gesture recognition to identify coughs, sneezes, vomiting, etc. Alternatively, or in addition, microphones may be used to hear those sounds and identify these gestures. Having identified these pathogen-spreading gestures, UV light may be opportunistically applied to reduce the spread of aerosol and potentially disinfect droplets and aerosolized pathogens in the air. Similarly, in a bathroom setting, a microphone may be utilized to identify activity such as a toilet flushing or a sink or shower being used. These activities are known to generate aerosols. UV light may be applied to deactivate pathogens present in those aerosols. Cleaning crews may also be supplied with data regarding where pathogen-spreading gestures have occurred and dispatched to clean the affected areas.

In some embodiments, computer vision is utilized to identify surfaces contacted by a patient who has an infection. These surfaces are highlighted on a 2D or 3D map of the room and displayed on a graphical user interface (GUI) for healthcare workers to use when wiping using cleaning solutions and or disinfecting chemicals or other forms of physical disinfection.

In some embodiments, computer vision deployed in an office setting identifies the highest touch surfaces by observing contact between people and various surfaces (for example the corner of a desk). These surfaces are highlighted on a 2D or 3D map of the room and displayed on a GUI for janitorial surfaces to use when wiping using cleaning solutions. In some embodiments, a cleaning robot is tasked to clean these surfaces.

In some embodiments, computer vision is utilized to track peoples' movement and apply more UV light. For example, UV light is applied within a threshold limit value. In another example, UV light is applied with sufficient dose to reduce specific organisms by certain desired log reductions. UV light is applied to areas and surfaces (e.g., desks, keyboards, etc.) of greater activity and thus reduces surface borne transmission. The system may reduce light to areas with less traffic and surface contact, thereby preserving lamp life. Depending on the orientation of the light, the system may apply greater UV irradiation to reduce airborne pathogens. Through AI predictive analysis and modeling, the system may anticipate where infections might occur by looking at human traffic patterns and ensure that those areas receive greater levels of UV and attention from cleaning staff.

In some embodiments, human traffic patterns are utilized to recommend the best locations for installing UV devices within a room. This recommendation is based on the most trafficked paths and surfaces, and the access of UV light to those places.

In some embodiments, a sensor is provided that is capable of periodically both counting the people in a room while also determining if each person is wearing a mask. That information is used over time to compute an estimation of human respiratory activity. That estimation is combined with calculations using other physical characteristics of the environment of the gathering space such as room volume, ventilation characteristics, temperature and humidity, to compute an estimate of concentration of possible pathogens in the space. The device may determine much or all of the relevant inputs to the computation using its own sensing and inference capabilities.

In some embodiments, information from mobile phones is utilized by the system to enhance and improve the estimate of respiratory activity by incorporating details about the individuals as provided by the mobile device. The mobile phone data could include user contact tracking data, medical data, and recent activities. Such estimates could help individuals, management teams, health teams, governments, and infectious disease researchers better understand the risks and results of group gatherings. Coupled with information about individual behavior and contacts such devices would enhance the value of efforts to trace contacts and limit the spread of pathogens. UV and manual cleaning can be applied as determined is necessary or helpful to reduce the potential spread of pathogens.

In some embodiments, the position of people is tracked. For example, the system notes that a person is at a cubicle; and notes that if they were not there, that could be tracked and noted as potential sick day. The system uses this information to see how such absent people interacted with other people and adjust disinfection profiles accordingly.

Identify Coordinates of Areas

The cleaning crew may need to return to room 100 to clean spots that it didn't clean the first time. These missed spots are the consequences of the various efforts to clean. Information on these areas may be provided so that the crew can know exactly where to focus their follow-up cleaning efforts.

The first step is to compute coordinates of these missed spots. FIG. 8 depicts table 800 comprising rows of coordinates in accordance with some embodiments. Each row of table 800 corresponds to a point in space in room 100 relative to UV device 210. For example, row 810 corresponds to X, Y, Z coordinates (2, 1.5, 2). This point corresponds to one point of missed spot 121, also shown as missed spots 521 and 621 in FIGS. 5 and 6, respectively. Other rows of table 800 correspond to the other points that define the shape of missed spot 121.

In some embodiments, the points in space stored in the rows of table 800 for a missed spot track the boundaries of said spot with precision. In another embodiment, said points roughly identify the missed spots using a simple shape, such as circles, rectangles, triangles, etc., the shape of which includes the entire missed spot.

Pictures of Rooms with Areas Overlaid

Figure 9:
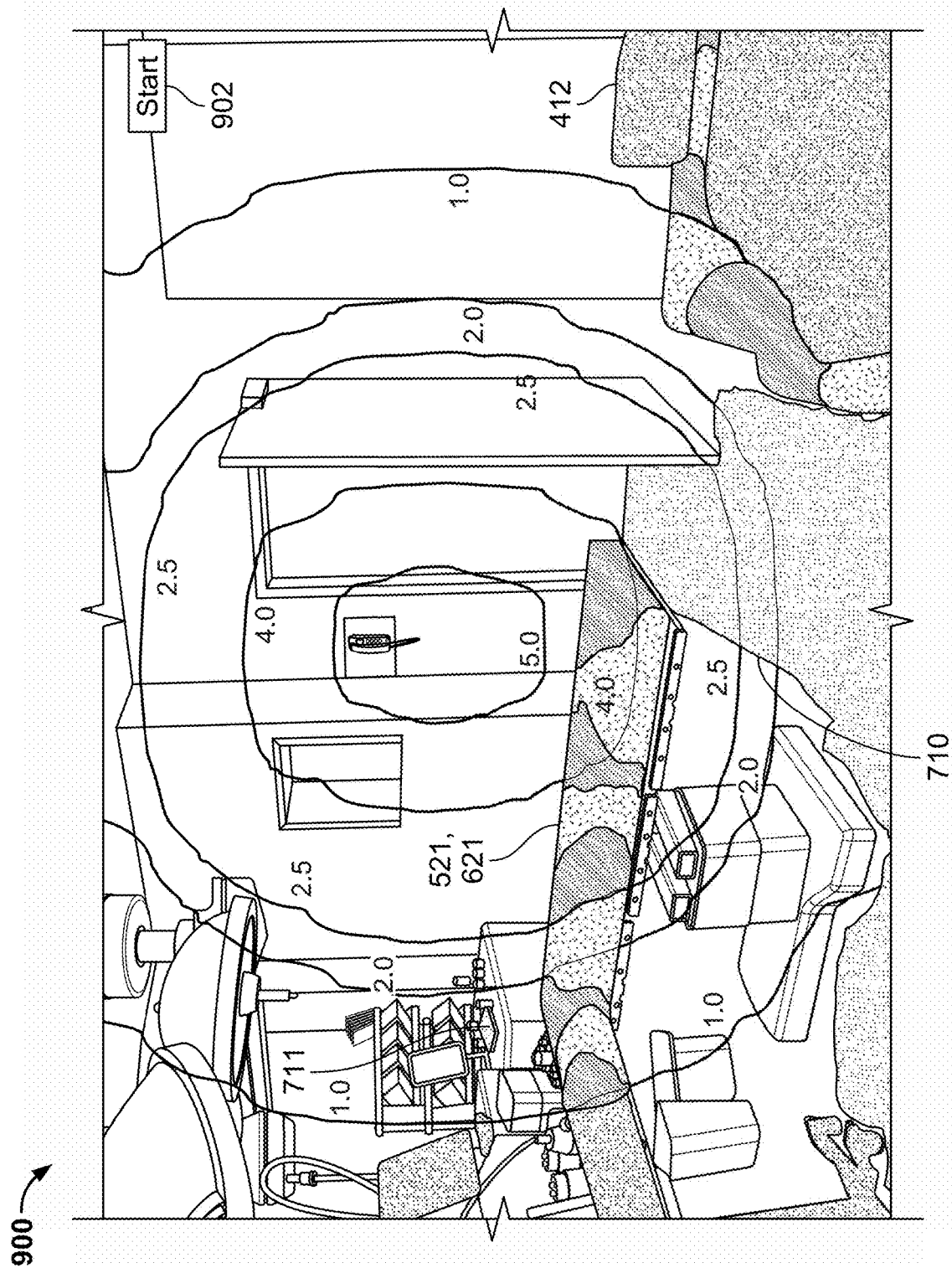
FIG. 9 depicts an image of a room with the missed spots identified in various colors in accordance with some embodiments.

The coordinates of the surfaces within a space may be determined during an installation process of device 400 within room 100. Once the coordinates of the areas have been computed, the next step involves using these coordinates and overlaying the determined coordinates over the coordinates of the surfaces within the space to prepare one or more images of room 100, with the areas highlighted. FIG. 9 depicts image 900 of room 100 with the missed spots identified in various colors.

In some embodiments, image 900 is presented in a mobile application that the cleaners, including cleaner 110, have access to via their mobile phones, tablets, and other such devices or on a page printed with the image(s). Using image 900, the cleaning crew can quickly re-clean only the missed spots identified by image 900.

In some embodiments, multiple camera devices are deployed in room 100, or a stereoscopic camera is used, providing different perspectives of the room. In these embodiments, the mobile app creates a 3D map of room 100, which the cleaner can manipulate to see from different angles and perspectives. The mobile app enables the ability to zoom in on a surface from different angles. Such features are known in the art of mobile app development.

Image 900 shows red areas, including missed spots 521, 621. These areas are colored red since they are identified as the areas missed by the human cleaners on their most recent effort to clean room 100.

Area 412 is shaded pink to indicate it is a low UV dose area. Such areas might require additional disinfection by any form of disinfection (e.g., further UV exposure, sending a person or robot to manually use chemical disinfectants, etc.).

The nature of the surface can also be selected by the user or the camera can use machine learning to determine which surfaces are of interest. For example, it is unlikely a person will manually clean the ceiling if it receives a low dose, however a keyboard or a door knob for example might be identified as surfaces that require further disinfection if they are in zones of lower irradiation. Additionally, surfaces that have an underside that is obscured from the light could be identified by machine learning and workers or robots could be sent to clean these areas.

Footpath 710 and surface 711 are shaded blue to indicate they are high traffic areas; the former with footfalls, the latter with hand touches.

Image 900 may include a "start" button 902 that one or more cleaners of the cleaning crew press on the GUI of a device when they start the re-cleaning. This alerts the computer vision technology that the current cleaning effort is a re-cleaning rather than an original cleaning.

In some embodiments, the system automatically determines when the cleaners are engaged in a re-cleaning effort rather than an original cleaning. The system starts a countdown timer at the moment it sends image 900 to the mobile apps of the cleaners. The length of this timer can be defined as the time pathogens can reproduce or the time that a patient could effectively shed pathogens or re-contaminate a room through contact. Alternatively, the length of the timer can be set by an administrator of room 100.

If cleaners arrive at room 100 within the defined countdown time, the system assumes that the present cleaning effort is a re-cleaning process. Otherwise, the system assumes the cleaning effort is an original one with the entire room being the subject of the effort.

Figure 10:
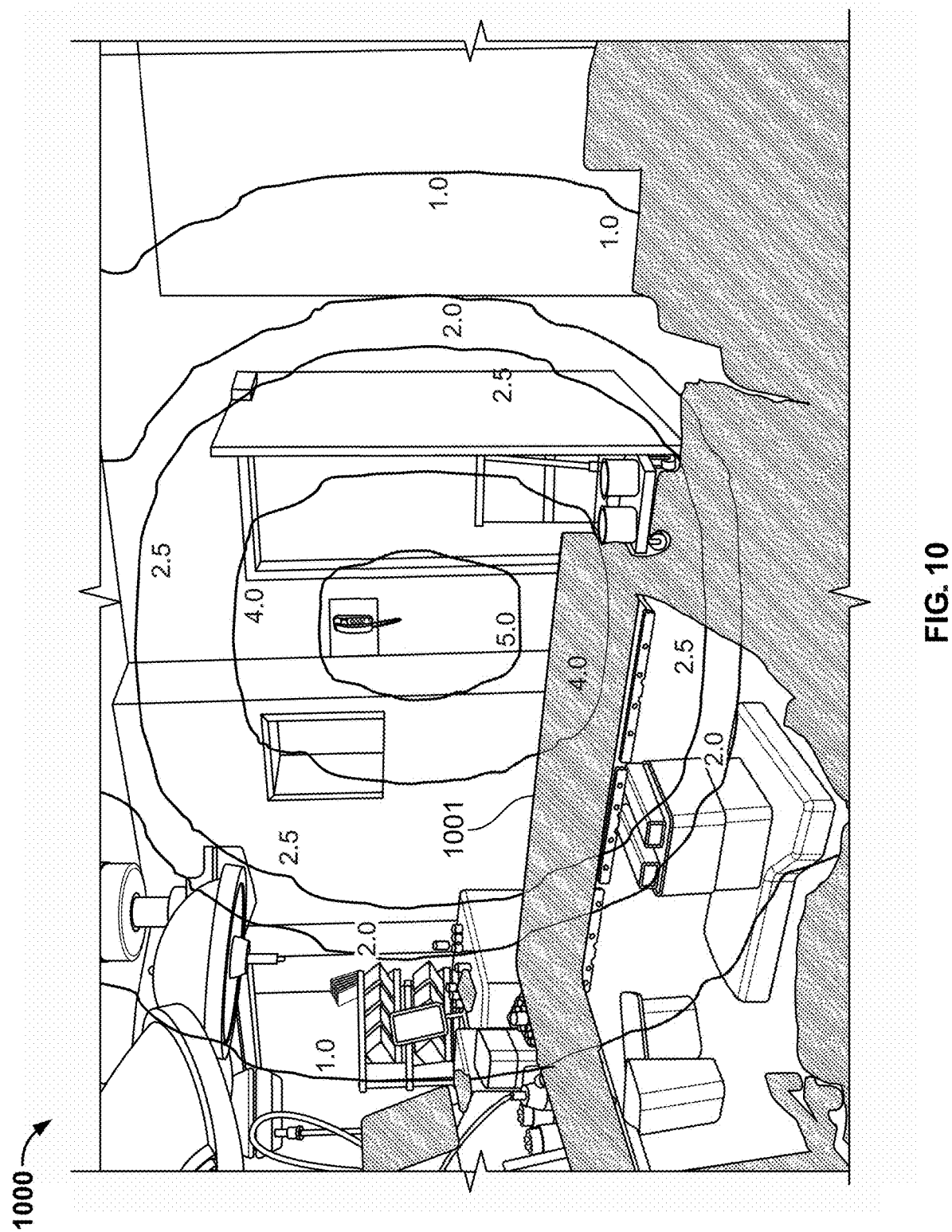
FIG. 10 depicts an image of a room with the re-cleaning effort completed in accordance with some embodiments.

In some embodiments, once the cleaners complete the re-cleaning of room 100, notification of this event is presented in their devices. FIG. 10 depicts image 1000 of room 100 with the re-cleaning effort completed in accordance with some embodiments. For example, the mobile app can do one or more of playing a sound indicating completion, and replacing image 900 with image 1000, showing fully re-cleaned room 100, with re-cleaned surfaces 1001 appearing in green.

In some embodiments, assessments of the cleaners are provided to the cleaners and their managers. This assessment can include a ranking of the cleaners according to different criteria such as completeness, speed, and a combination of the two, with different factors possibly having different weights for the assessment.

In some embodiments, "gamification" is provided and presented to the cleaning staff and their managers. For example, bonuses/recognition are provided to crews and workers that clean in the allotted time and minimize the need for recleaning.

In some embodiments, feedback on the efficacy of the cleaning effort is provided in real-time, in an attempt to avoid the need for a subsequent cleaning effort. Such feedback includes one or more of audible beeps, spoken voice, illumination such as a spot light pointing at an area or surface. Such feedback is presented on one or more of the mobile app, and/or a TV in the room (which could display any number of views along with instructions).

Figure 11:
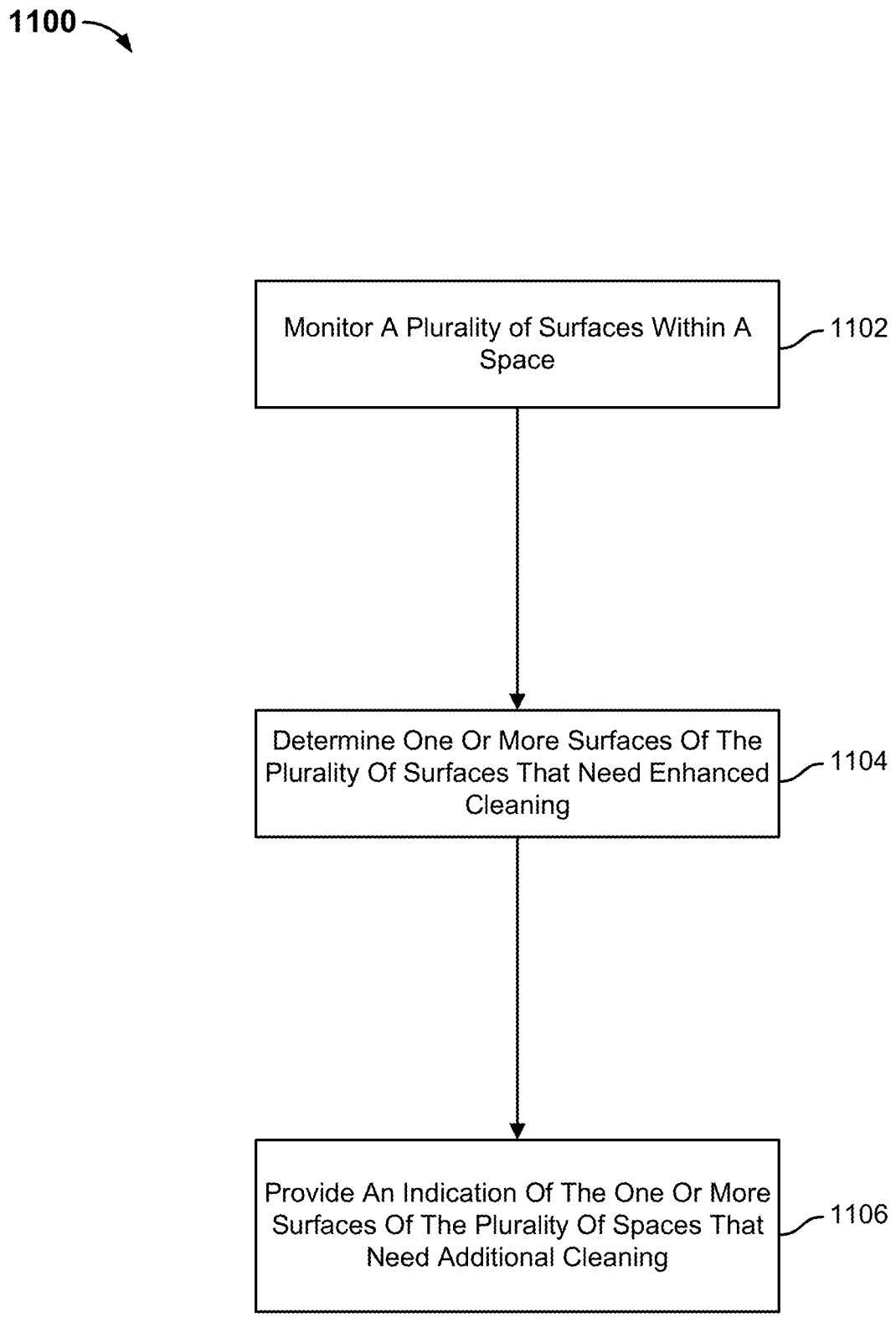
FIG. 11 depicts a flow diagram illustrating a process for providing enhanced artificial intelligence cleaning in accordance with some embodiments.

FIG. 11 depicts a flow diagram illustrating a process for providing enhanced artificial intelligence cleaning in accordance with some embodiments. In the example shown, process 1100 may be implemented by a device, such as device 400, or by a server, such as servers 1610, 1700.

At 1102, a plurality of surfaces within a space is monitored. A space may be a room, an elevator, a car, a train, a grocery store, a gym, a studio, a place of worship, a theater, or any other human occupied space. A surface may be associated with a table, a bed, a chair, a keyboard, a screen, a device, an appliance, a floor, a wall, a ceiling, a door, a fixture, or any other object within a space that may be contacted by an occupant.

The plurality of surfaces within the space is monitored using one or more devices. Each of the devices includes one or more UV lamps. Each of the devices may include one or more camera sensors. In some embodiments, a device is in communication with a camera sensor that is separate from the device. The device may employ computer vision based on the data provided by the one or more camera sensors.

In some embodiments, one or more camera sensors are in communication (wired or wireless) with a remote server. The remote server may monitor the space using computer vision based on the data provided by the one or more camera sensors.

At 1104, one or more surfaces that need enhanced cleaning are determined. A UV lamp of a device is associated with a field of illumination (e.g., a circle). A light dose associated with the UV lamp is strongest at a center of the field of illumination and weakest at the boundary of the field of illumination. Based on the data from the one or more camera sensors, computer vision is used to determine which surfaces (partial or entire surfaces) of the plurality of surfaces within the space that are near and/or outside the boundary of the field of illumination.

A cleaning crew of one or more cleaners may enter a space. Computer vision is used to monitor the cleaning crew during a cleaning of the space. In some embodiments, computer vision is used to determine that the cleaning crew missed an entire surface of an object located within the space. In some embodiments, computer vision is used to determine that the cleaning crew missed a partial surface of an object located within the space. In some embodiments, computer vision is used to determine that the cleaning crew cleaned an entire surface of an object located within the space.

A space may include one or more high traffic areas (e.g., door knob, floor, keyboard). Computer vision may be used to determine whether an area is a high traffic area based on an amount of time in which the area was occupied or touched since a previous cleaning. An area may be considered to be a high traffic area if the area was occupied by one or more occupants more than a threshold amount of time or touched more than a threshold number of times between cleanings.

In some embodiments, an area is considered to be a high traffic area based on historical data (e.g., historical data indicates that a certain portion of a floor within a space is frequently stepped on). In some embodiments, it is determined whether an area is a high traffic area based on the amount of traffic that area saw since a last cleaning. For example, an area may be considered to be a high traffic area after a first cleaning because the area was occupied by one or more occupants more than the threshold amount of time and a low traffic area after a second cleaning because the area was not occupied by one or more occupants more than the threshold amount of time.

At 1106, an indication of the one or more determined surfaces that require enhanced cleaning is provided. A cleaning crew may be provided with a device having a GUI. The GUI may provide a view of a space from one or more angles. In some embodiments, the GUI provides a view of a space from a single angle because there is a single UV device in the space. In some embodiments, the GUI provides a view of a space from multiple angles because there are multiple devices in the space (e.g., in opposite corners). In some embodiments, the view from the multiple angles is stitched together to provide a 3D rendering of the space. In the GUI, the indication may highlight the one or more determined surfaces that require enhanced cleaning.

The device or remote server may determine the one or more surfaces that require enhanced cleaning based on the determined surfaces (partial or entire surfaces) of the plurality of surfaces within the space that are near and/or outside the boundary of the field of illumination of the one or more devices, the one or more surfaces (partial or entire surfaces) that the cleaning crew missed, and the one or more determined high traffic areas. In some embodiments, for purposes of being thorough, a high traffic area is included in the indication, regardless of whether a previous cleaning crew cleaned the high traffic area. In some embodiments, an area determined to be near and/or outside a boundary of the field of illumination of a device is excluded from the indication because the previous cleaning crew cleaned that area.

Figure 12:
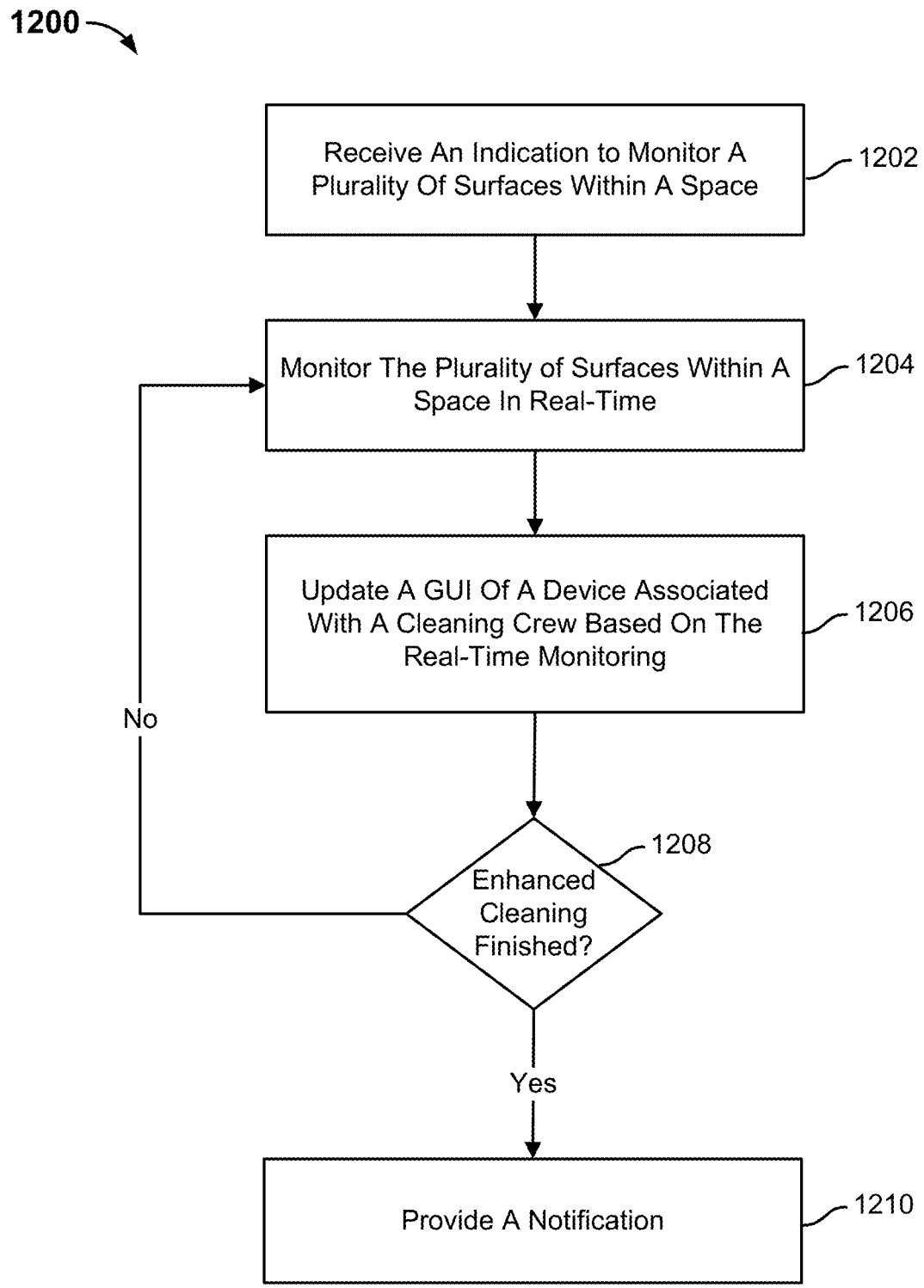
FIG. 12 depicts a flow diagram illustrating a process for providing enhanced artificial intelligence cleaning in accordance with some embodiments.

FIG. 12 depicts a flow diagram illustrating a process for providing enhanced artificial intelligence cleaning in accordance with some embodiments. In the example shown, process 1200 may be implemented by a device, such as device 400, or by a server, such as servers 1610, 1700.

At 1202, an indication to monitor a plurality of surfaces within a space is received. A GUI of a device associated with a cleaning crew may provide an indication of the one or more determined surfaces that require enhanced cleaning. The GUI may include a button that indicates the enhanced cleaning of the room is to begin and/or has ended.

At 1204, the plurality of surfaces within the space are monitored in real-time. In response to the button being selected, the one or more camera sensors associated with the space begin to provide data that is used for computer vision purposes. Computer vision is used to monitor the cleaning crew during the enhanced cleaning session.

At 1206, a GUI of a device associated with the cleaning crew is updated based on the real-time monitoring. Portions of the GUI are updated when the cleaning crew cleans a surface that needs enhanced cleaning. For example, a surface that was highlighted in red may be highlighted in green after the cleaning crew performs enhanced cleaning on the surface.

At 1208, it is determined whether an enhanced cleaning of the space is finished. For example, the enhanced cleaning of the space may be determined to be finished when all of the non-green highlighted surfaces shown in FIG. 9 are highlighted in green as shown in FIG. 10. In response to a determination that the cleaning is finished, process 1200 proceeds to 1210. In response to a determination that the cleaning of the space is not finished, process 1200 returns to 1204.

At 1210, a notification is provided. The notification may be provided to management associated with the cleaning crew or space. The notification may indicate that the enhanced cleaning of the room is completed, an amount of time needed to perform the enhanced cleaning, which of the cleaners (if more than one person in a cleaning crew) performed a majority of the cleaning, an efficacy associated with each of the one or more cleaners, whether a surface required additional cleaning even after an enhanced cleaning was performed, etc.

Figure 13A:
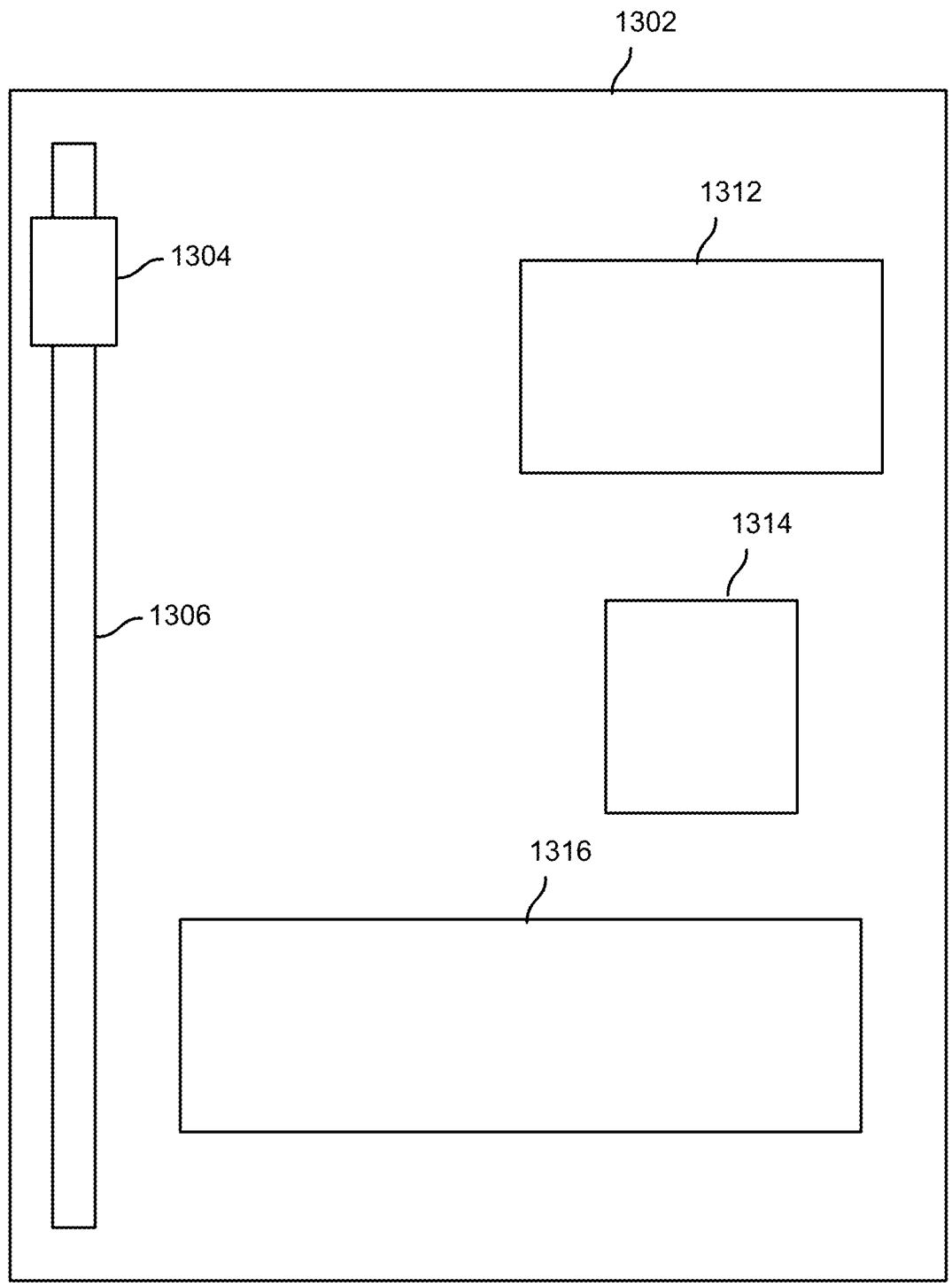
FIG. 13A depicts a block diagram of a space in accordance with some embodiments.
Figure 13B:
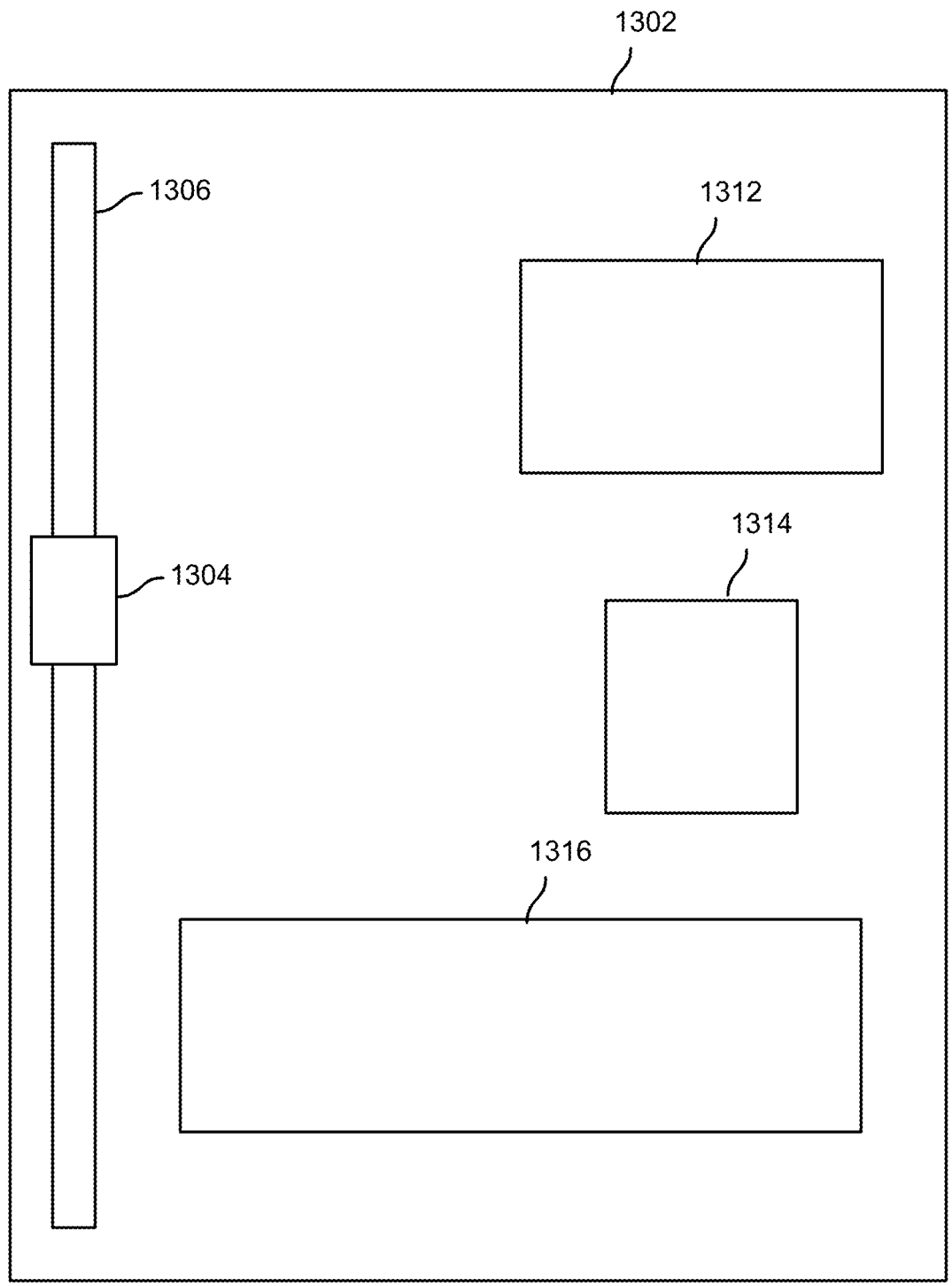
FIG. 13B depicts a block diagram of a space in accordance with some embodiments.

FIG. 13A depicts a block diagram of a space in accordance with some embodiments. In the example shown, space 1302 includes a device 1304 located on a rail 1306. Device 1304 may include one or more UV lights. A position of device 1304 may be adjusted to any position on rail 1306 modify a field of illumination of device 1304. Space 1302 also includes a first object 1312 having a first surface, a second object 1314 having a second surface, and a third object 1316 having a third surface. As seen in FIG. 13B, the position of device 1304 has been adjusted from a first position to a second position. In some embodiments, the position of the device 1304 is manually adjusted. In some embodiments, the position of the device 1304 is mechanically adjusted in response to a command. The command may be received from an operator or a server. In some embodiments, the position and field of illumination associated with device 1304 is automatically adjusted, based on one or more commands received from a server, to a plurality of positions to clean all of the surfaces that are reachable by the field of illumination associated with device 1304 and located within space 1302.

Figure 14:
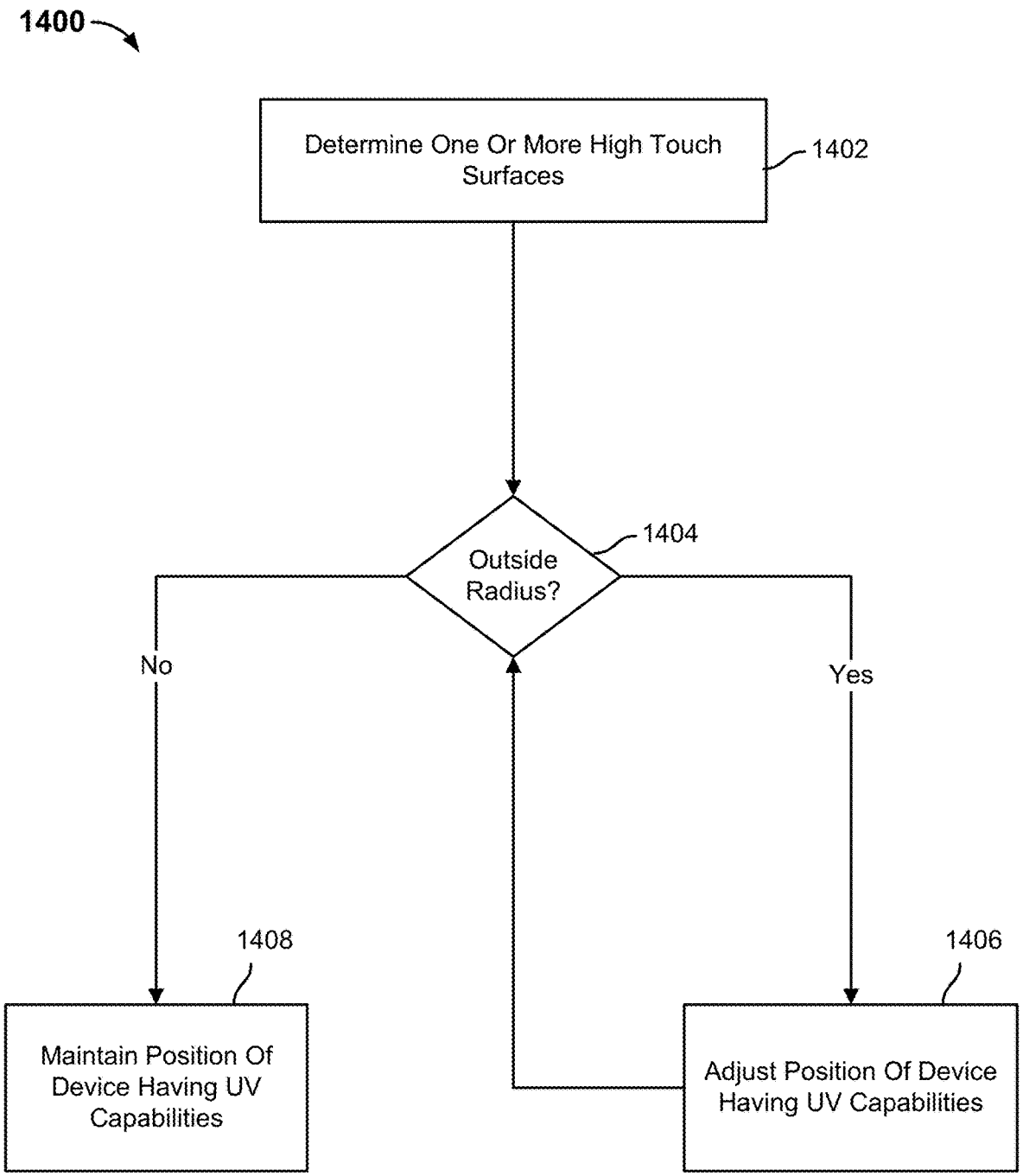
FIG. 14 depicts a flow diagram of a process for optimizing a position of a UV device in a space in accordance with some embodiments.

FIG. 14 depicts a flow diagram of a process for optimizing a position of a device having UV light capabilities in a space in accordance with some embodiments. In the example shown, process 1400 may be implemented by a device, such as device 400, or by a server, such as servers 1610, 1700.

At 1402, one or more high touch surfaces are determined. A high touch surface may be determined based on an amount of contact a surface encounters between cleanings. A surface may be determined to be a high touch surface in response to determining that the amount of contact that the surface encounters between cleanings is greater than a threshold amount over a threshold period (e.g., more than a threshold amount of contact between several cleanings). Through AI predictive analysis and modeling, the one or more high touch surfaces may be determined by analyzing historical human traffic patterns within the space.

At 1404, it is determined whether at least one of one or more high touch surfaces is outside a radius of illumination associated with a device having UV capabilities (e.g., one or more UV lamps). In response to a determination that at least one of the one or more high touch surfaces are outside the radius of illumination associated with the device having UV capabilities, process 1400 proceeds to 1406. In response to a determination that at least one of the one or more high touch surfaces is not outside the radius of illumination associated with the device having UV capabilities, process 1400 proceeds to 1408.

At 1406, a position of the device having UV capabilities is adjusted. The position of the device having UV capabilities may be recommended by an AI model that analyzes the historical cleaning data associated with a space, that is, the AI model may recommend the position of the device having UV capabilities is adjusted such that a center of the device's field of illumination is over most of or an entire high touch surface.

In some embodiments, adjusting a position of the device having UV capabilities creates a conflict because when the device is located at a first position, a first high touch surface may be within an illumination radius associated with the device having UV capabilities and a second high touch surface may not be within the illumination radius associated with the device. When the position of the device is adjusted from the first position to the second position, the first high touch surface may not be within the illumination radius associated with the device and the second high touch surface may be within the illumination radius associated with the device. In such embodiments, a machine learning model may utilize historical data to determine which surface among the first high touch surface and the second high touch surface is more likely to need enhanced cleaning. A surface may be more likely to need enhanced cleaning because the surface is a high frequency touch area or cleaners do not sufficiently clean the surface (either partially or entirely).

At 1408, a position of the device having UV capabilities is maintained.

Figure 15:
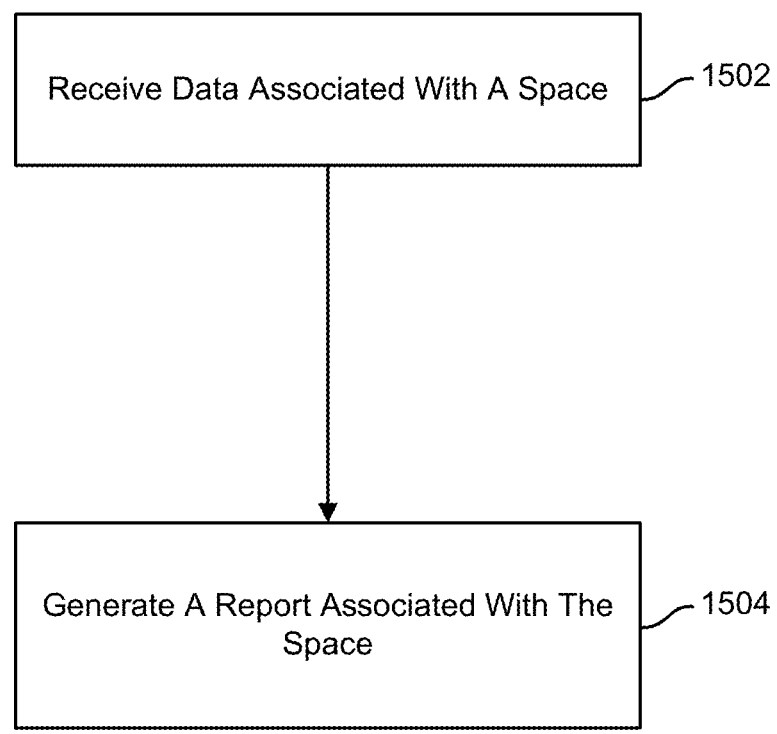
FIG. 15 depicts a flow diagram of a process for generating a report associated with a space in accordance with some embodiments.

FIG. 15 depicts a flow diagram of a process for generating a report associated with a space in accordance with some embodiments. In the example shown, process 1500 may be implemented by a device, such as device 400, or by a server, such as servers 1610, 1700. The server may be an on-prem server, a remote server, a cloud server, or other type of server.

At 1502, data associated with a space is received. The space may include one or more devices, such as device 400. The data is received from the one or more devices.

A device may include one or more camera sensors. The device may utilize the data outputted by the one or more camera sensors to perform preprocessing, feature extraction, machine learning, object detection/recognition, scene understanding, execute an application, and/or real-time processing of visual data. The data received from a device of the one or more devices may be an output of the device performing one or more of preprocessing, feature extraction, machine learning, object detection/recognition, scene understanding, executing an application and/or real-time processing of visual data.

An occupant is monitored while being present in a space. The occupant may have an ID tag that has an RFID tag. A device or server may determine an identity of the occupant based on reading the RFID tag while the occupant is in the space. In some embodiments, facial recognition is used to identify and monitor the occupant while being present in the space (e.g., cleaning, providing health care services, etc.). In some embodiments, the device can use other factors to identify a person or type of person, e.g., patient, staff, visitor, based on clothing, gestures, gait, or other factors.

At 1504, a report associated with the space is generated. In some embodiments, the report is an auditing report (e.g., a Joint Commission Report). The auditing report may require certain information to be disclosed. The server may utilize the received information to auto-generate the auditing report. For example, the auditing report may include information associated with the activity of a cleaning crew, alarms, alerts, heat maps, etc.

In some embodiments, the occupant wants to know their total dose of UV, the system produces a regular report showing a unique ID for each person, the location (e.g. room), the time of day, and the UV radiation dose received by the person. Reviewing such report, the person (e.g. nurse) can identify themselves by their knowledge of their own movements during the day. This allows the person to learn their unique ID, and search the report for that ID.

In some embodiments, the occupant is a cleaner and the cleaning habits associated with the cleaner are determined based on a monitoring of the cleaner using computer vision. The report may indicate the cleaning habits associated with the cleaner, such as one or more surfaces that the cleaner frequently misses. The report may provide one or more statistics associated with a cleaner, such as an amount of time spent cleaning a space.

In some embodiments, the report is a training document. Data associated with the space may be received according to a schedule (e.g., daily, after a cleaning crew has finished a cleaning session, etc.). Historical data associated with the space may be analyzed to identify one or more surfaces that are consistently missed, require additional cleaning (e.g., portions of the surface were not cleaned), and/or are effectively cleaned. The training document may be generated based on an analysis of the historical data associated with the space and provided to a cleaning crew associated with the space. The training document may identify the one or more surfaces that are consistently missed, require additional cleaning, and/or are usually effectively cleaned. The training document may be provided in an electronic (e.g., displayed on a device) or physical (e.g., paper) format. The training document may provide a checklist of the one or more surfaces within the room with which the cleaning is to clean. The training document may go into detail describing how to clean specific surfaces or pieces of equipment; it could also describe certain areas on pieces of equipment that are often missed and describe how they should be cleaned. The training document could also provide recommended contact times or completion times for various pieces of equipment and/or surfaces.

Figure 16:
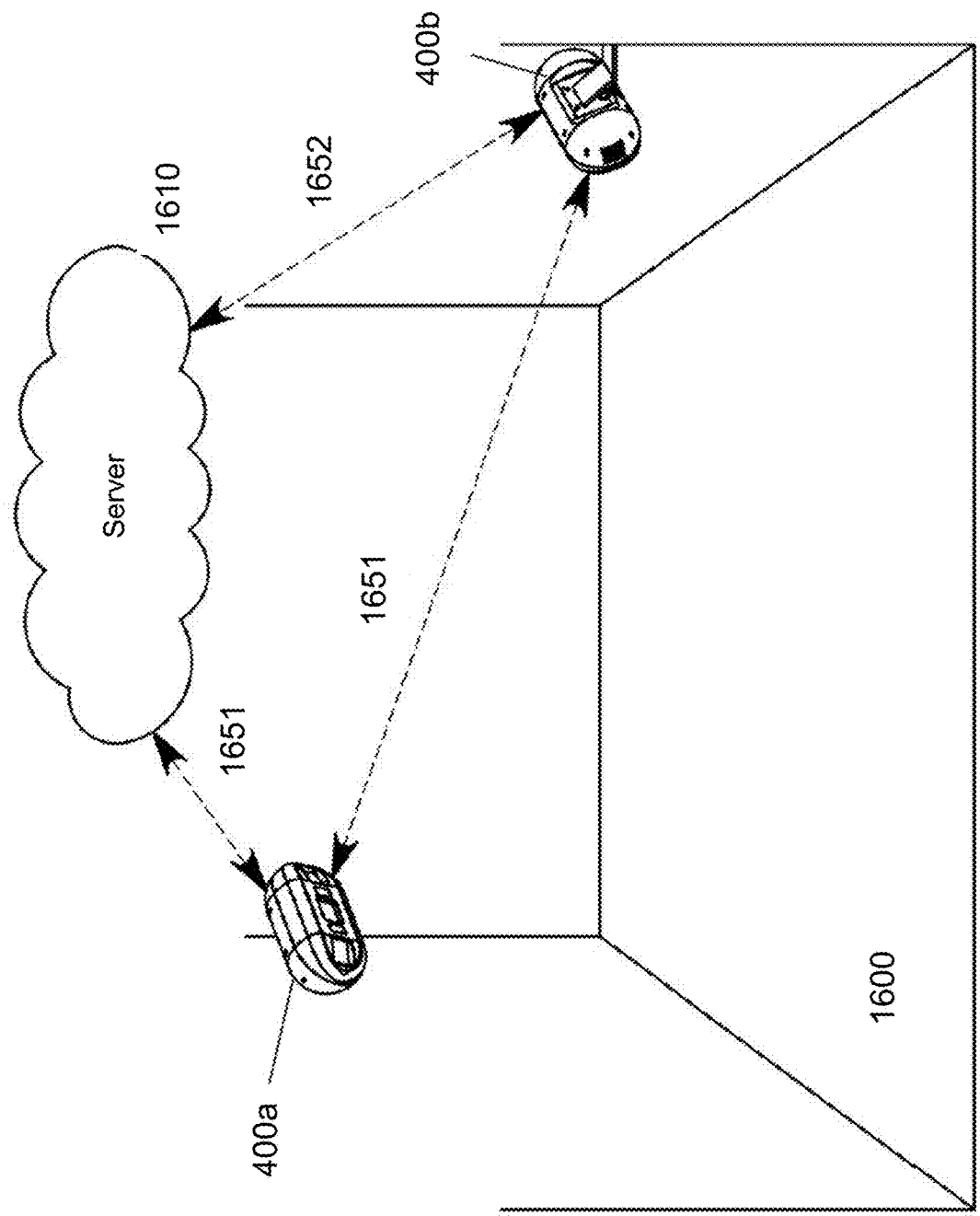
FIG. 16 depicts two devices within a space communicating with each other and with a server in accordance with some embodiments.

FIG. 16 depicts two devices within a space communicating with each other and with server 1610 in accordance with some embodiments. FIG. 16 shows a space 1600 in which two devices, 400a and 400b, are mounted in opposite corners of space 1600, in elevated positions. Server 1610 is located locally, or remotely on a network such as the Internet. Devices 400a and 400b may each communicate with server 1610 via data transmission paths 1651 and 1652, respectively. Device 400a and 400b may also communicate directly with each other via data transmission path 1641.

Local communications between devices 400a and 400b, as well as between each of device 400a and 400b with local server 1610 may be performed by wireless or wired technologies known in the art, for example, one or more of Ethernet, WiFi, and Bluetooth.

Remote communication between each of device 400a and 400b with remote server 1610 is performed by wireless technologies known in the art, for example, cellular and Internet.

One class of information communicated by one or more of devices 400a and 400b to server 1610 is data such as UV Level received by occupants, be it individuals identified by facial recognition or by wearables or simply people identified as mobile or static. Nurses, doctors (all healthcare workers) and visitors are considered to be mobile occupants. Mobile occupants will not be exposed to greater than 20 mj/cm^2 in 15 minutes. Patients are considered to be static occupants. Patients' faces will not be exposed to greater than 161 mj/cm^2 over 8 hours. The light sources from all devices either co-located or independent will be controlled to maintain these UV Levels.

Another class of information communication by one or more devices 400a and 400b to server 1610 is camera sensor data, which enables server 1610 to determine the efficacy of a cleaning crew.

Figure 17:
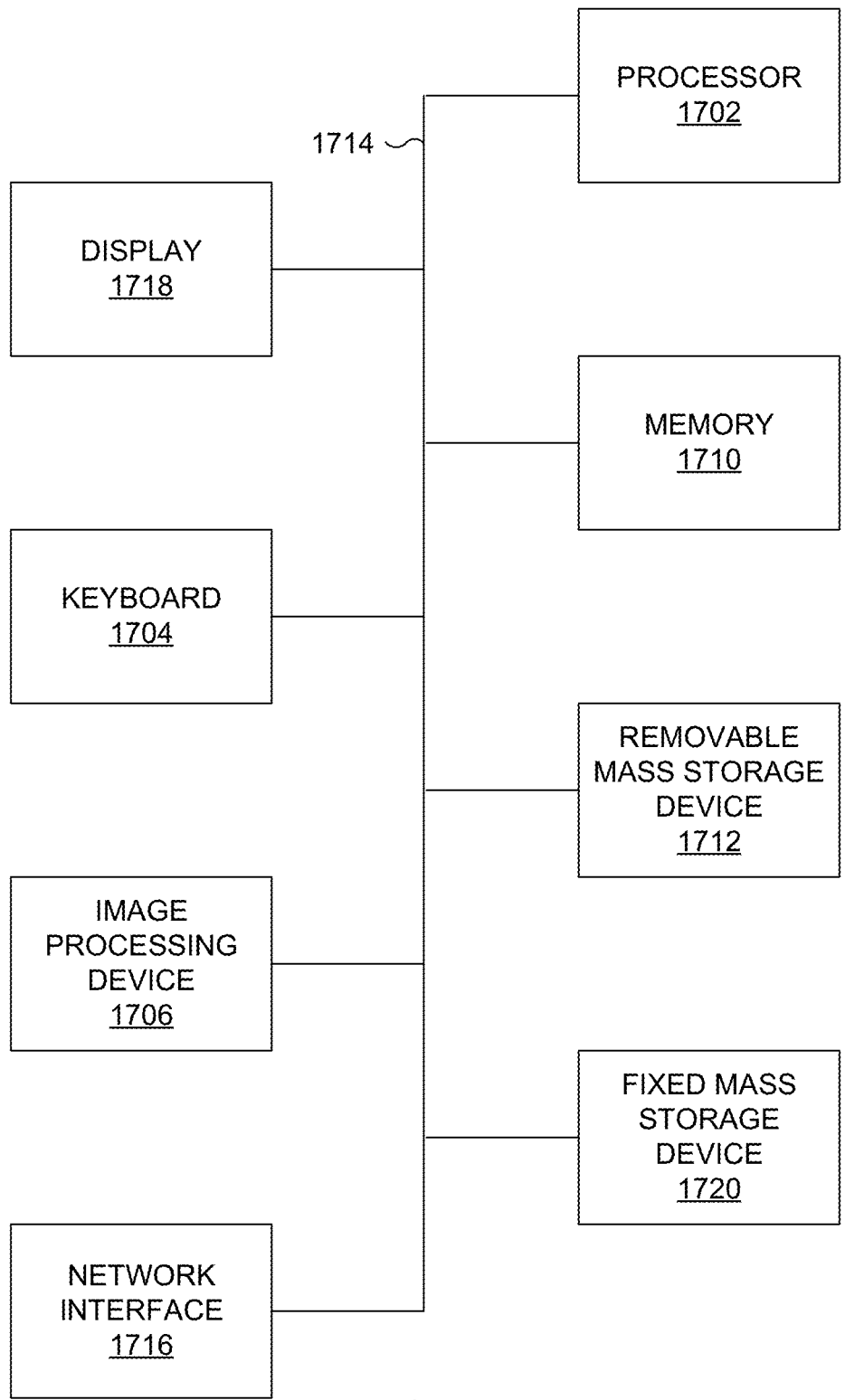
FIG. 17 is a functional diagram illustrating a server for AI enhanced cleaning in accordance with some embodiments.

FIG. 17 is a functional diagram illustrating a server for AI enhanced cleaning in accordance with some embodiments. As will be apparent, other server architectures and configurations can be used to perform the described product generation technique. Server 1700, which includes various subsystems as described below, includes at least one microprocessor subsystem (also referred to as a processor or a central processing unit (CPU) 1702). For example, processor 1702 can be implemented by a single-chip processor or by multiple processors. In some embodiments, processor 1702 is a general purpose digital processor that controls the operation of the server 1700. In some embodiments, processor 1702 also includes one or more coprocessors or special purpose processors (e.g., a graphics processor, a network processor, AI processor, etc.). Using instructions retrieved from memory 1710, processor 1702 controls the reception and manipulation of input data received on an input device (e.g., image processing device 1706, I/O device interface 1704), and the output and display of data on output devices (e.g., display 1718).

Processor 1702 is coupled bi-directionally with memory 1710, which can include, for example, one or more random access memories (RAM) and/or one or more read-only memories (ROM). As is well known in the art, memory 1710 can be used as a general storage area, a temporary (e.g., scratch pad) memory, and/or a cache memory. Memory 1710 can also be used to store input data and processed data, as well as to store programming instructions and data, in the form of data objects and text objects, in addition to other data and instructions for processes operating on processor 1702. Also as is well known in the art, memory 1710 typically includes basic operating instructions, program code, data, and objects used by the processor 1702 to perform its functions (e.g., programmed instructions). For example, memory 1710 can include any suitable computer readable storage media described below, depending on whether, for example, data access needs to be bi-directional or uni-directional. For example, processor 1702 can also directly and very rapidly retrieve and store frequently needed data in a cache memory included in memory 1710.

A removable mass storage device 1712 provides additional data storage capacity for the server 1700, and is optionally coupled either bi-directionally (read/write) or uni-directionally (read only) to processor 1702. A fixed mass storage 1720 can also, for example, provide additional data storage capacity. For example, storage devices 1712 and/or 1720 can include computer readable media such as magnetic tape, flash memory, PC-CARDS, portable mass storage devices such as hard drives (e.g., magnetic, optical, or solid state drives), holographic storage devices, and other storage devices. Mass storages 1712 and/or 1720 generally store additional programming instructions, data, and the like that typically are not in active use by the processor 1702. It will be appreciated that the information retained within mass storages 1712 and 1720 can be incorporated, if needed, in standard fashion as part of memory 1710 (e.g., RAM) as virtual memory.

In addition to providing processor 1702 access to storage subsystems, bus 1714 can be used to provide access to other subsystems and devices as well. As shown, these can include a display 1718, a network interface 1716, an input/output (I/O) device interface 1704, an image processing device 1706, as well as other subsystems and devices. For example, image processing device 1706 can include a camera, a scanner, etc.; I/O device interface 1704 can include a device interface for interacting with a touchscreen (e.g., a capacitive touch sensitive screen that supports gesture interpretation), a microphone, a sound card, a speaker, a keyboard, a pointing device (e.g., a mouse, a stylus, a human finger), a Global Positioning System (GPS) receiver, an accelerometer, and/or any other appropriate device interface for interacting with system 1700. Multiple I/O device interfaces can be used in conjunction with server 1700. The I/O device interface can include general and customized interfaces that allow the processor 1702 to send and, more typically, receive data from other devices such as keyboards, pointing devices, microphones, touchscreens, transducer card readers, tape readers, voice or handwriting recognizers, biometrics readers, cameras, portable mass storage devices, and other computers.

The network interface 1716 allows processor 1702 to be coupled to, another computer, one or more robotic systems, computer network, a network of storage bins, or telecommunications network using a network connection as shown. For example, through the network interface 1716, the processor 1702 can receive information (e.g., data objects or program instructions) from another network, or output information to another network in the course of performing method/process steps. Information, often represented as a sequence of instructions to be executed on a processor, can be received from and outputted to another network. An interface card or similar device and appropriate software implemented by (e.g., executed/performed on) processor 1702 can be used to connect the server 1700 to an external network and transfer data according to standard protocols. For example, various process embodiments disclosed herein can be executed on processor 1702, or can be performed across a network such as the Internet, intranet networks, or local area networks, in conjunction with a remote processor that shares a portion of the processing. Additional mass storage devices (not shown) can also be connected to processor 1702 through network interface 1716.

In addition, various embodiments disclosed herein further relate to computer storage products with a computer readable medium that includes program code for performing various computer-implemented operations. The computer readable medium includes any data storage device that can store data which can thereafter be read by a server. Examples of computer readable media include, but are not limited to: magnetic media such as disks and magnetic tape; optical media such as CD-ROM disks; magneto-optical media such as optical disks; and specially configured hardware devices such as application-specific integrated circuits (ASICs), programmable logic devices (PLDs), and ROM and RAM devices. Examples of program code include both machine code as produced, for example, by a compiler, or files containing higher level code (e.g., script) that can be executed using an interpreter.

The server shown in FIG. 17 is but an example of a server suitable for use with the various embodiments disclosed herein. Other servers suitable for such use can include additional or fewer subsystems. In some servers, subsystems can share components (e.g., for touchscreen-based devices such as smart phones, tablets, etc., I/O device interface 1704 and display 1718 share the touch sensitive screen component, which both detects user inputs and displays outputs to the user). In addition, bus 1714 is illustrative of any interconnection scheme serving to link the subsystems. Other computer architectures having different configurations of subsystems can also be utilized.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A system, comprising:
   a plurality of sensors; and
   a processor configured to:
   monitor in real-time during a cleaning of a space a plurality of surfaces within the space utilizing data outputted from the plurality of sensors;
   utilize computer vision to develop scene understanding by processing the data associated with the plurality of sensors, wherein the scene understanding includes interpreting relations between the plurality of surfaces and one or more people within the space, wherein interpreting relations between the plurality of surfaces and the one or more people within the space includes drawing corresponding shapes around the plurality of surfaces and portions of the one or more people within the space;

track movement of the corresponding shapes of the portions of the one or more people with respect to the corresponding shapes of the plurality of surfaces;

determine one or more surfaces of the plurality of surfaces that need additional cleaning based on the tracked movement of the corresponding shapes of the portions of the one or more people with respect to the corresponding shapes of the plurality of surfaces; and provide a notification of the one or more determined surfaces that need the additional cleaning.

2. The system of claim 1, wherein the plurality of sensors include a camera sensor, a thermal sensor, an infrared sensor, a lidar sensor, and/or a radar sensor.

3. The system of claim 1, wherein the computer vision tracks corresponding movement of the one or more people within the space.

4. The system of claim 1, wherein locations of the corresponding movement of the one or more people within the space are recorded.

5. The system of claim 1, wherein the processor is configured to utilize the computer vision to determine that an entire surface of a first surface of the plurality of surfaces was not cleaned.

6. The system of claim 1, wherein the processor is configured to utilize the computer vision to determine that a portion of a first surface of the plurality of surfaces was not cleaned.

7. The system of claim 1, wherein the processor is configured to utilize the computer vision to determine that an entire surface of a first surface of the plurality of surfaces was cleaned.

8. The system of claim 1, wherein based in part on the computer vision, the notification includes one or more areas of the plurality of surfaces that need the additional cleaning.

9. The system of claim 1, wherein the notification includes an efficacy associated with the cleaning of the space.

10. The system of claim 1, wherein the notification is provided in a graphical user interface that color codes the one or more determined surfaces that need the additional cleaning.

11. The system of claim 1, wherein the cleaning of the space is performed by the one or more people within the space.

12. The system of claim 11, wherein corresponding cleaning habits of the one or more people within the space are determined based on the real-time monitoring.

13. The system of claim 12, wherein the processor is configured to generate a report based on the real-time monitoring.

14. The system of claim 13, wherein the report identifies a first subset of surfaces of the plurality of surfaces that are consistently missed, a second subset of surfaces of the plurality of surfaces that require the additional training, and/or a third subset of surfaces of the plurality of surfaces that are effectively cleaned.

15. A method, comprising:

monitoring in real-time during a cleaning of a space a plurality of surfaces within the space utilizing data outputted from a plurality of sensors;

utilizing computer vision to develop scene understanding by processing the data associated with the plurality of sensors, wherein the scene understanding includes interpreting relations between the plurality of surfaces and one or more people within the space, wherein interpreting relations between the plurality of surfaces and the one or more people within the space includes drawing corresponding shapes around the plurality of surfaces and portions of the one or more people within the space;

tracking movement of the corresponding shapes of the portions of the one or more people with respect to the corresponding shapes of the plurality of surfaces;

determining one or more surfaces of the plurality of surfaces that need additional cleaning based on the tracked movement of the corresponding shapes of the portions of the one or more people with respect to the corresponding shapes of the plurality of surfaces; and providing a notification of the one or more determined surfaces that need the additional cleaning.

16. The method of claim 15, wherein the plurality of sensors include a camera sensor, a thermal sensor, an infrared sensor, a lidar sensor, and/or a radar sensor.

17. The method of claim 15, wherein the computer vision is utilized to determine that an entire surface of a first surface of the plurality of surfaces was not cleaned.

18. The method of claim 15, wherein the computer vision is utilized to determine that a portion of a first surface of the plurality of surfaces was not cleaned.

19. The method of claim 15, wherein the computer vision is utilized to determine that an entire surface of a first surface of the plurality of surfaces was cleaned.

20. A computer program product embodied in a non-transitory computer readable medium and comprising computer instructions for:

monitoring in real-time during a cleaning of a space a plurality of surfaces within the space utilizing data outputted from a plurality of sensors;

utilizing computer vision to develop scene understanding by processing the data associated with the plurality of sensors, wherein the scene understanding includes interpreting relations between the plurality of surfaces and one or more people within the space, wherein interpreting relations between the plurality of surfaces and the one or more people within the space includes drawing corresponding shapes around the plurality of surfaces and portions of the one or more people within the space;

tracking movement of the corresponding shapes of the portions of the one or more people with respect to the corresponding shapes of the plurality of surfaces;

determining one or more surfaces of the plurality of surfaces that need additional cleaning based on the tracked movement of the corresponding shapes of the portions of the one or more people with respect to the corresponding shapes of the plurality of surfaces; and providing a notification of the one or more determined surfaces that need the additional cleaning.

\* \* \* \* \*